US010578552B2

(12) United States Patent
Kimura et al.

(10) Patent No.: US 10,578,552 B2
(45) Date of Patent: Mar. 3, 2020

(54) SCATTERING TOMOGRAPHY METHOD AND SCATTERING TOMOGRAPHY DEVICE

(71) Applicants: National University Corporation Kobe University, Hyogo (JP); Integral Geometry Science Inc., Hyogo (JP)

(72) Inventors: Kenjiro Kimura, Hyogo (JP); Noriaki Kimura, Hyogo (JP)

(73) Assignees: INTEGRAL GEOMETRY SCIENCE INC., Hyogo (JP); KENJIRO KIMURA, Hyogo (JP)

( * ) Notice: Subject to any disclaimer, the term of this patent is extended or adjusted under 35 U.S.C. 154(b) by 245 days.

(21) Appl. No.: 14/767,094

(22) PCT Filed: Feb. 12, 2014

(86) PCT No.: PCT/JP2014/000722
§ 371 (c)(1),
(2) Date: Aug. 11, 2015

(87) PCT Pub. No.: WO2014/125815
PCT Pub. Date: Aug. 21, 2014

(65) Prior Publication Data
US 2015/0377778 A1 Dec. 31, 2015

(30) Foreign Application Priority Data
Feb. 12, 2013 (JP) .................. 2013-025043

(51) Int. Cl.
*A61B 6/03* (2006.01)
*G01N 21/47* (2006.01)
(Continued)

(52) U.S. Cl.
CPC ............. *G01N 21/47* (2013.01); *G01N 22/00* (2013.01); *G01N 22/02* (2013.01);
(Continued)

(58) Field of Classification Search
CPC ...... G01N 22/02; A61B 6/4233; A61B 6/5205
(Continued)

(56) References Cited

U.S. PATENT DOCUMENTS 4,598,366 A * 7/1986 Devaney ............ G01S 15/8977
128/916
5,715,819 A 2/1998 Svenson et al.
(Continued)

FOREIGN PATENT DOCUMENTS

JP 8-54379 2/1996
JP 8-304538 11/1996
(Continued)

OTHER PUBLICATIONS

Monte et al., "Radio Frequency Tomography for Tunnel Detection", IEEE Transactions on Geophysics and Remote Sensing, vol. 48, No. 3, Mar. 2010, pp. 1128-1137.*
(Continued)

*Primary Examiner* — Thomas L Dickey
(74) *Attorney, Agent, or Firm* — Wenderoth, Lind & Ponack, L.L.P.

(57) ABSTRACT

A scattering tomography method includes: radiating waves to an object from transmitting antenna elements arranged on a curved surface; receiving scattered waves by receiving antenna elements arranged on the curved surface; and reconstructing an image relating to the information on the interior of the object from scattered wave data representing the scattered waves received by the receiving antenna elements, and in the reconstructing, a function $\phi$ for reconstructing the image relating to the information on the interior of the object is set in advance, an equation which a fundamental scattered function satisfies is constructed, a visualization function $\rho$ that is obtained by solving the equation is derived from the scattered wave data, and the image relating to the informa-
(Continued)

tion on the interior of the object is reconstructed using the visualization function.

6 Claims, 10 Drawing Sheets

(51) Int. Cl.
| | | |
|---|---|---|
| *G01N 29/46* | (2006.01) | |
| *G01N 22/02* | (2006.01) | |
| *G01N 29/06* | (2006.01) | |
| *G01S 15/89* | (2006.01) | |
| *G01N 22/00* | (2006.01) | |

(52) U.S. Cl.
CPC ..... *G01N 29/0654* (2013.01); *G01N 29/0672* (2013.01); *G01N 29/46* (2013.01); *G01S 15/8977* (2013.01); *G01N 2201/12* (2013.01); *G01N 2291/0289* (2013.01)

(58) Field of Classification Search
USPC .............................................................. 22/2
See application file for complete search history.

(56) References Cited

U.S. PATENT DOCUMENTS

| | | | |
|---|---|---|---|
| 6,005,916 | A | 12/1999 | Johnson et al. |
| 6,253,100 | B1 | 6/2001 | Zhdanov |
| 6,873,569 | B2 | 3/2005 | Vernet et al. |
| 6,876,878 | B2 | 4/2005 | Zhdanov |
| 7,550,969 | B2 | 6/2009 | Zhdanov |
| 8,583,393 | B2 | 11/2013 | Kitazawa et al. |
| 8,838,405 | B2 | 9/2014 | Kitazawa et al. |
| 2002/0062074 | A1 | 5/2002 | Zhdanov |
| 2004/0004906 | A1 | 1/2004 | Vernet et al. |
| 2004/0167396 | A1* | 8/2004 | Chambers ................. A61B 8/08 600/425 |
| 2006/0241409 | A1 | 10/2006 | Winters et al. |
| 2009/0119040 | A1 | 5/2009 | Zhdanov |
| 2009/0293621 | A1 | 12/2009 | Kitazawa et al. |
| 2012/0010493 | A1* | 1/2012 | Semenov ............. A61B 5/0507 600/407 |
| 2012/0137778 | A1 | 6/2012 | Kitazawa et al. |
| 2014/0035911 | A1 | 2/2014 | Kitazawa et al. |

FOREIGN PATENT DOCUMENTS

| | | |
|---|---|---|
| JP | 10-504893 | 5/1998 |
| JP | 2003-177656 | 6/2003 |
| JP | 2004-512117 | 4/2004 |
| JP | 2004-141447 | 5/2004 |
| JP | 2009-276319 | 11/2009 |
| JP | 2009-288129 | 12/2009 |
| WO | 95/28883 | 11/1995 |
| WO | 95/32665 | 12/1995 |
| WO | 02/35254 | 5/2002 |

OTHER PUBLICATIONS

Woodward, "Wave-equation tomography: I", published in Geophysics, vol. 57, No. 1, Jan. 1992, 24 pages.*
Secrest, "Basic Principles of Ultrasonography", Veternary Technician, Dec. 2006 (vol. 27, No. 12).*
"All About Transducer Arrays" downloaded Aug. 6, 2018.*
Meaney et al., "A Clinical Prototype for Active Microwave Imaging of the Breast", p. 1841, IEEE Transactions on Microwave Theory and Techniques, vol. 48, No. 11, Nov. 2000 (Year: 2000).*
Meaney et al., "Microwave Image Reconstruction Utilizing Log-Magnitude and Unwrapped Phase to Improve High-Contrast Object Recovery", p. 104, IEEE Transactions on Medical Imaging, vol. 20, No. 2, Feb. 2001 (Year: 2001).*
Golnabi et al., "Threedimensional microwave imaging with incorporated prior structural information," Proc. SPIE 8317, Medical Imaging 2012: Biomedical Applications in Molecular, Structural, and Functional Imaging, 83171L (Apr. 16, 2012); doi: 10.1117/12.910738 (Year: 2012).*
Fear, "Microwave Imaging of the Breast", Technology in Cancer Research & Treatment vol. 4, pp. 69-82, Feb. (2005) (Year: 2005).*
O'Halloran et al., "Rotating Antenna Microwave Imaging System for Breast Cancer Detection", Progress in Electromagnetics Research, vol. 107, 203-217, 2010 (Year: 2010).*
Extended European Search Report dated Oct. 28, 2015 in corresponding European Patent Application No. 14751867.4.
Natterer, F., "Imaging and Inverse Problems of Partial Differential Equations," 2006, pp. 1-22.
Semenov, Serguei, "Microwave tomography: review of the progress towards clinical applications," Phil. Trans. R. Soc. A, 2009, pp. 3021-3042, XP-002661164.
International Search Report (ISR) dated May 20, 2014 in International (PCT) Application No. PCT/JP2014/000722.
Kazuaki Ezawa et al., "Development of the 3D Imaging Radar for Inspection of Tunnel Lining Concrete", Mitsui Zousen Giho, No. 184, p. 24, Feb. 2005, together with English abstract.
Kazuyuki Nakahata et al., "Development of flaw shape imaging method using ultrasonic linear array transducer", The Japan Society of Mechanical Engineers, JSME annual meeting 2005(1), pp. 679-680, Sep. 2005, together with English abstract.
Kazuyuki Nakahata et al., "Ultrasonic Imaging of Internal Flaw with Flexible Array Transducer Located on Irregular Surface", The Institute of Electronics, Information and Communication Engineers, IEICE Technical Report, Jun. 2012, together with English abstract.
Kenjiro Kimura et al., "Tunnel Juki Teiko Koka Soshi o Mochiita Ko Bunkaino Concrete Naibu Tekkin Kensa Gijutsu ni Kansuru Kenkyu (Development of high-resolution magnetic imaging method with tunneling magnetoresistance device for inspecting reinforcing steels inside concrete building)", The Japanese Society for Non-Destructive Inspection Koen Taikai Koen Gaiyoshu, Heisei 24 Nendo Shunki, The Japanese Society for Non-Destructive Inspection, pp. 89-92, May 22, 2012, together with English partial translation.
Japanese Office Action dated Oct. 31, 2017 in Japanese Patent Application No. 2015-500144 (with partial English translation).
Takashi Takenaka, "Inverse Scattering Analysis Based on Optimization Techniques", The Institute of Electronics, Information and Communication Engineers, Proceedings of the 2011 Electronics Society Conference 1, Japan, 2011, S1-2.
Takashi Takenaka, "Microwave Tomography", The Institute of Electronics, Information and Communication Engineers, Technical Report, Japan, 2011, vol. 111, No. 341, pp. 49-54 (with English abstract).

\* cited by examiner

Max.Frequency = 3.2 GHz
Depth = 200mm, 500mm, $\Delta z$ = curvfactor · dy/4

Definition
Defined as curvfactor = N*L / (2R)
when it is assumed that a sensor array is arranged on a parabola N is the number of y-axis sensors (= NY)
L is total length of sensor array (= N*dy)
R is radius of curvature
dx is x-axis scanning pitch
dy is y-axis sensor-to-sensor distance curvfactor = 4.68

Depth = 200 mm curvfactor = 4.68

Depth = 500 mm

Planar MPLA Radar
curvfactor = 0
Depth = 500 mm

MPCLA RadarIV
curvfactor = 0
Depth = 500 mm

Planar MPLA Radar
curvfactor = 7.02
Depth = 500 mm

MPCLA RadarIV
curvfactor = 7.02
Depth = 500 mm

Planar MPLA Radar curvfactor = 14.04

Depth = 500 mm

MPCLA RadarIV curvfactor = 14.04

Depth = 500 mm

SCATTERING TOMOGRAPHY METHOD AND SCATTERING TOMOGRAPHY DEVICE

TECHNICAL FIELD

The present invention relates to technology for obtaining and visualizing (imaging) information on the interior of an object using waves, and particularly to a scattering tomography method and a scattering tomography device in which a wave scattering phenomenon is used.

BACKGROUND ART

Conventionally, x-ray computed tomography (CT) (x-ray tomography), magnetic resonance imaging (MRI), positron emission tomography (PET), and other methods are used to visualize information on the interior of an object such as a biological body and a building. Specifically, electromagnetic waves such as light, terahertz waves, millimeter waves, and microwaves, or phonon-like waves such as ultrasonic waves, sound waves, and elastic waves are radiated to a biological body or an object that is to be observed, or are radiated to plasma, and resultant scattered waves (reflected waves) are observed and analyzed to visualize information on the interior of the biological body, the interior of the object, or the interior of the plasma. Recently, instead of waves, an electromagnetic field is also used to visualize information on the interior of a biological body or an object.

Generally, these methods adopt a technique in which waves u such as electromagnetic waves or ultrasonic waves are radiated to an object O, scattered waves p that are waves scattered by the object O are observed in multiple places around the object O, and resultant data is visualized (for example, refer to Patent Literatures (PTLs) 1 to 3 and Non Patent Literatures (NPLs) 1 to 3).

In the technique disclosed in PTL 1, information on the interior of an object is visualized using radio waves. For the visualization, data on scattered waves observed with a sensor arranged on the circumference of a circle is repeatedly obtained while the data is modified using a parameter such as electrical conductivity or a dielectric constant.

The technique disclosed in PTL 2 is the ultrasound phased array technique. In this technique, data on ultrasonic waves received by an ultrasonic sensor is modified using a mean vector and is visualized.

In the technique disclosed in PTL 3, ultrasonic waves are radiated in a plane to an object to visualize data on ultrasonic waves received by a sensor. Information on the interior of an object in a curved shape is visualized using an increased number of observed data items or using approximation or modification, for example.

The technique disclosed in NPL 1 is a technique related to a multi-path linear array radar and allows information on a flaw or the like inside concrete to be visualized. In this technique, a sensor is arranged on a surface of an object to observe scattered waves of radiated waves, and observed data is analyzed and visualized.

The technique disclosed in NPL 2 allows information on the interior of an object to be visualized using ultrasonic waves. In this technique, scattered waves are observed when ultrasonic waves are radiated to an object, and observed data is visualized by way of the Born approximation (the Kirchhoff Approximation).

In the technique disclosed in NPL 3, scattered waves obtained by a sensor arranged on a curved surface are observed, and time waveform data obtained for each sensor is compared with previously obtained data and is visualized.

CITATION LIST

Patent Literature

[PTL 1] Japanese Unexamined Patent Application Publication No. 2003-177656
[PTL 2] Japanese Unexamined Patent Application Publication No. 2009-288129
[PTL 3] Japanese Unexamined Patent Application Publication No. 2004-512117

Non Patent Literature

[NPL 1] Development of the 3D Imaging Radar for Inspection of Tunnel Lining Concrete, MITSUI ZOSEN TECHNICAL REVIEW No. 184, p. 24, February, 2005
[NPL 2] Development of flaw shape imaging method using ultrasonic linear array transducer, Transactions of the Japan Society of Mechanical Engineers, p. 679, September, 2005
[NPL 3] Ultrasonic Imaging of Internal Flaw with Flexible Array Transducer Located on Irregular Surface, IEICE (Institute of Electronics, Information and Communication Engineers) technical report, June, 2012

SUMMARY OF INVENTION

Technical Problem

A scattering phenomenon occurring when waves are radiated to an object can be expressed using an operator. For example, using an operator A, a physical equation can be expressed as $p = A_u[O]$ where O is an object, u is radiated waves, and p is observed data. When the object O, the radiated waves u, and the operator (system function) A are known, the problem to solve the observed data p is called the forward problem. The forward problem is a mathematically well-established approach and can be solved with a method in a standard physics textbook.

On the other hand, an important issue in medical or industrial fields is a problem to solve what the object O is when the radiated waves u, the system function A, and the observed data p are known. This problem is called the inverse problem in the sense that the causal relation of a physical phenomenon is traced in an inverse direction, and can be expressed as $O = A_u^{-1}[p]$. This inverse problem is applied in a method of visualizing information on the interior of an object by observing and analyzing scattered waves when waves are radiated to the object (the scattering tomography).

The inverse problem is not a mathematically well-established approach—there has been no established theory for the inverse problem as of yet—unlike the forward problem, and thus is problematic not being easy to solve. Accordingly, in a method of visualizing information on the interior of an object using the inverse problem, it is necessary to reacquire data after changing the theory, internal device configuration, etc., or to modify acquired data every time the condition, such as a curved shape of the object, changes, for example. For this reason, the method of visualizing information on the interior of an object using the inverse problem is difficult to use in a versatile manner. In addition, there are also problems of a low calculation speed and high memory usage due to the need to reacquire or modify data.

Thus, an object of the present invention is to provide a scattering tomography method and a scattering tomography device by which the inverse problem is analyzed in a versatile manner at high speed so that information on the interior of an object can be visualized in a simple, convenient manner.

Solution to Problem

In order to solve the above-described problem, a scattering tomography method according to one aspect of the present invention is a scattering tomography method for analyzing scattered waves of waves radiated to an object and comprises: radiating the waves to the object from a plurality of transmitting antenna elements arranged on a curved surface; receiving the scattered waves by a plurality of receiving antenna elements arranged on the curved surface; and reconstructing an image relating to information on an interior of the object using, as a boundary condition, scattered wave data representing the scattered waves received by the receiving antenna elements, wherein in the reconstructing: a function $\phi$ for reconstructing the image relating to the information on the interior of the object is set in advance, the function $\phi$ being defined in later-stated Expression 5; an equation which the function $\phi$ satisfies is constructed, the equation being defined in later-stated Expression 10; a visualization function $\rho$ that is obtained by solving the equation is derived from the scattered wave data, the visualization function $\rho$ being defined in later-stated Expression 24, the scattered wave data being obtained by measurement; and the image relating to the information on the interior of the object is reconstructed using the visualization function $\rho$.

Furthermore, a scattering tomography method according to one aspect of the present invention is a scattering tomography method for analyzing scattered waves of waves radiated to an object and comprises: radiating the waves to the object from a plurality of transmitting antenna elements arranged on a curved surface; receiving the scattered waves by a plurality of receiving antenna elements arranged on the curved surface; and reconstructing an image relating to information on an interior of the object from scattered wave data representing the scattered waves received by the receiving antenna elements, wherein in the reconstructing: a function $\phi$ for reconstructing the image relating to information on the interior of the object is set in advance, the function $\phi$ being defined in later-stated Expression 27; an equation which the function $\phi$ satisfies is constructed, the equation being defined in later-stated Expression 39; a visualization function $\rho$ that is obtained by solving the equation is derived from the scattered wave data, the visualization function $\rho$ being defined in later-stated Expression 52, the scattered wave data being obtained by measurement; and the image relating to the information on the interior of the object is reconstructed using the visualization function $\rho$.

With this, the function $\phi$ is set for three-dimensional space in the reconstructing, allowing information on the interior of an object having a curved surface with high curvature to be more accurately visualized at high speed.

With this, a partial differential equation for the inverse problem is set in an analytical model in which a sensor is arranged on an arbitrary curved surface, and solving this equation allows information on the interior of an object having a curved surface with high curvature to be visualized in a versatile manner at high speed.

Furthermore, the visualization function may be derived using a fast Fourier transform.

With this, analysis data can be obtained at high speed, allowing information on the interior of an object to be visualized at high speed.

Furthermore, the waves may be electromagnetic waves or ultrasonic waves.

With this, information on the interior of an object having a curved surface with high curvature can be visualized in a versatile, simple, and convenient manner.

Furthermore, the waves may be pulsed waves or periodic waves having a predetermined frequency.

With this, information on the interior of an object having a curved surface with high curvature can be visualized in a versatile, simple, and convenient manner.

In order to solve the above-described problem, a scattering tomography device according to one aspect of the present invention is a scattering tomography device for analyzing scattered waves of waves radiated to an object and comprises: a plurality of transmitting antenna elements that are arranged on a curved surface and radiate the waves to the object; a plurality of receiving antenna elements that are arranged on the curved surface and receive the scattered waves which are the radiated waves after having been scattered in the object; and an image reconstructor that reconstructs an image relating to information on an interior of the object from scattered wave data representing the received scattered waves, wherein the image reconstructor: sets in advance a function $\phi$ for reconstructing the image relating to the information on the interior of the object, the function $\phi$ being defined in later-stated Expression 5; constructs an equation which the function $\phi$ satisfies, the equation being defined in later-stated Expression 10; derives, from the scattered wave data, a visualization function $\rho$ that is obtained by solving the equation, the scattered wave data being obtained by measurement, the visualization function $\rho$ being defined in later-stated Expression 24; and reconstructs, using the visualization function $\rho$, the image relating to the information on the interior of the object.

With this, a partial differential equation for the inverse problem is set in an analytical model in which a sensor is arranged on an arbitrary curved surface, and solving this equation allows information on the interior of an object having a curved surface with high curvature to be visualized in a versatile manner at high speed.

Furthermore, a scattering tomography method according to one aspect of the present invention is a scattering tomography device for analyzing scattered waves of waves radiated to an object and comprises: a plurality of transmitting antenna elements that are arranged on a curved surface and radiate the waves to the object; a plurality of receiving antenna elements that are arranged on the curved surface and receive the scattered waves which are the radiated waves after having been scattered in the object; and an image reconstructor that reconstructs an image relating to information on an interior of the object from scattered wave data representing the received scattered waves, wherein the image reconstructor: sets in advance a function $\phi$ for reconstructing the image relating to the information on the interior of the object, the function $\phi$ being defined in later-stated Expression 27; constructs an equation which the function $\phi$ satisfies, the equation being defined in later-stated Expression 39; derives, from the scattered wave data, a visualization function $\rho$ that is obtained by solving the equation, the scattered wave data being obtained by measurement, the visualization function $\rho$ being defined in later-stated Expression 52; and reconstructs, using the visualization function $\rho$, the image relating to the information on the interior of the object.

With this, the function φ is set for three-dimensional space in the reconstructing, allowing information on the interior of an object having a curved surface with high curvature to be more accurately visualized at high speed.

Furthermore, the image reconstructor may derive the visualization function using a fast Fourier transform.

With this, analysis data can be obtained at high speed, allowing information on the interior of an object to be visualized at high speed.

Furthermore, the waves may be electromagnetic waves or ultrasonic waves.

With this, information on the interior of an object having a curved surface with high curvature can be visualized in a versatile, simple, and convenient manner.

Furthermore, the waves may be pulsed waves or periodic waves having a predetermined frequency.

With this, information on the interior of an object having a curved surface with high curvature can be visualized in a versatile, simple, and convenient manner.

Advantageous Effects of Invention

According to the present invention, the inverse problem is analyzed in a versatile manner at high speed so that information on the interior of an object can be visualized in a simple, convenient manner.

DESCRIPTION OF EMBODIMENTS

Underlying Knowledge Forming the Basis of the Present Invention

A technique forming the basis of the present invention is described below prior to describing embodiments of the present invention.

Figure 1:
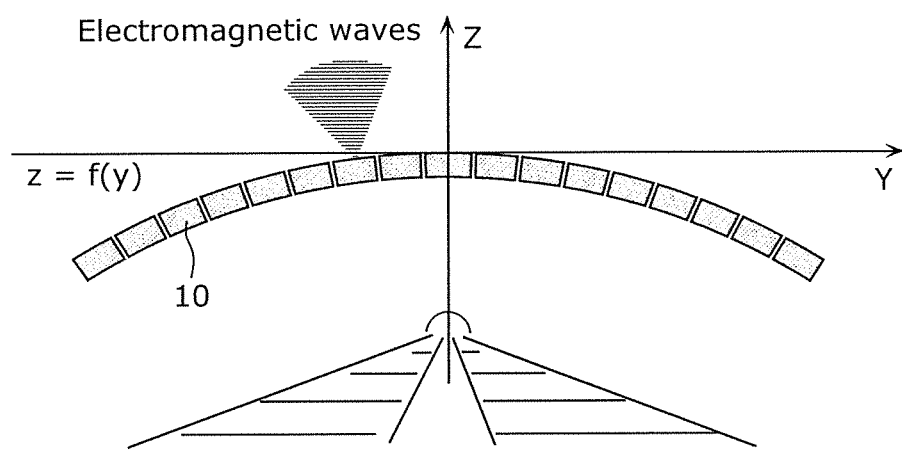
FIG. 1 is an analysis model for explaining a technique forming the basis of the present invention.
Figure 2:
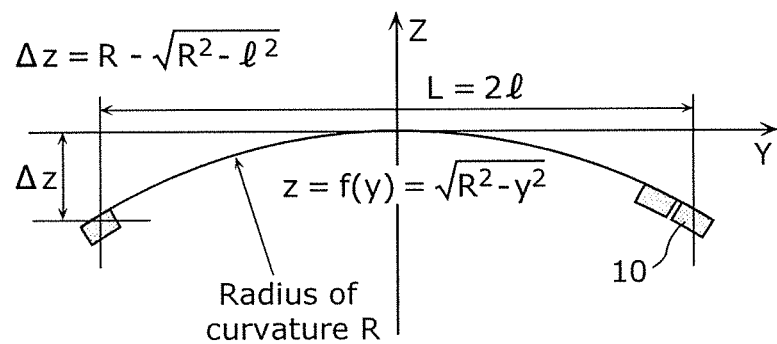
FIG. 2 is a simplified illustration of the analysis model in FIG. 1.

FIG. 1 and FIG. 2 are illustration for explaining about a technique forming the basis of the present invention.

As an example of the above-described method of detecting a flaw or the like of an object using scattered waves of radiated waves in a non-destructive manner (the scattered tomography), a multi-path linear array radar (MPLA radar) is available. In this method, for example, antenna elements 10 are attached as a sensor to an object, such as a tunnel, and electromagnetic waves are radiated from the antenna elements 10 as illustrated in FIG. 1, reflected waves (scattered waves) that are the electromagnetic waves reflected in the object are detected by the antenna elements 10, and a flaw or the like of the object is detected based on a relationship between the radiated electromagnetic waves and the reflected waves in a non-destructive manner.

As illustrated in FIG. 2, the MPLA radar performs calculation through approximation assuming that an object has a flat surface even when the object has a curved surface with curvature. This means that the theory of the MPLA radar is established on the premise that the antenna elements 10 are aligned in a plane, and therefore a problem of the MPLA radar is that when the antenna elements 10 are arranged on a curved surface with high curvature, an image obtained by calculation may not be in focus due to an increased error that affects the phase of electromagnetic waves.

Accordingly, when the object has such low curvature (a large radius of curvature) as a tunnel for Shinkansen bullet trains (having a radius of curvature of approximately 4.8 m), an error of the calculation through the approximation assuming that the object has a flat surface is small and does not cause a problem, whereas, when the object has such high curvature (a small radius of curvature) as a tunnel for Zairaisen local trains (having a radius of curvature of 2.2 to 2.8 m), the calculation through the approximation assuming that the object has a flat surface is hardly reliable.

Depending on a combination of a transmitter and a receiver on the antenna, the calculation through the approximation assuming that the object has a flat surface has a problem in that the phase may have an error equivalent to not less than one wavelength. For example, in the analysis model of FIG. 2, assume that a relative dielectric constant E of a material configuring the tunnel is 6.0, the array size L is 1000 mm, the effective wavelength A of radio waves is 20.4 mm, and the highest frequency of the radio waves is 3

GHz, the error Δz occurring in the approximation when the tunnel for Zairaisen local trains has a radius R of 2.2 m is 57.6 mm, which is about three times the effective wavelength of radio waves.

Therefore, the following describes a multi-path curviLinear array radar (MPCLA radar), which is an improvement of the MPLA radar and represents scattering tomography that allows for detection of a flaw or the like with reduced error even when the object has high curvature. With the MPCLA radar, the inverse problem is analyzed in a versatile manner at high speed so that information on the interior of an object can be visualized in a simple, convenient manner.

Hereinafter, embodiments of the present invention are described with reference to the Drawings. Note that the same or like structural elements share the same reference symbols in the Drawings.

Each of the following embodiments describes a specific preferred example of the present invention. The numerical values, shapes, materials, structural elements, the arrangement and connection of the structural elements, steps, the processing order of the steps etc., shown in the following embodiments are mere examples, and therefore do not limit the present invention. Therefore, among the structural elements in the following embodiments, structural elements not recited in any one of the independent claims which indicate the broadest concepts of the present invention are described as arbitrary structural elements in a more preferred embodiment.

Generally, the scattering tomography represents a method of detecting a flaw or the like of an object using scattered waves of radiated waves in a non-destructive manner. In order to clarify that the scattering tomography is a method, this method is hereinbelow referred to as a scattering tomography method. A device for performing the scattering tomography method is hereinbelow referred to as a scattering tomography device.

Embodiment 1

Configuration of Sensor Array

Embodiment 1 is described in which a one-dimensional sensor array is used as a sensor for performing the scattering tomography method. The one-dimensional sensor array includes a transmitting antenna element and a receiving antenna element arranged in one dimension (a linear array antenna).

In this embodiment, to cite an example of visualizing information on the interior of tunnel lining concrete, a situation is described where each of (i) transmitting antenna elements and (ii) receiving antenna elements included in the linear array antenna forms one line (in one dimension) on a part of a tunnel along the circumferential direction, and the linear array antenna is subject to translational scanning in the tunnel depth direction.

First, a configuration of a multi-path array radar 20 which is a scattering tomography device according to this embodiment is described. The multi-path array radar 20 is a linear array antenna in which a plurality of antenna elements for transmission are arranged in a line and a plurality of antenna elements for reception are arranged in a line. In this linear array antenna, an arbitrary element in the transmitting antenna element line transmits waves, and an arbitrary element in the receiving antenna element line receives reflected waves. For example, when $n_y$ transmitting antenna elements and $n_y$ receiving antenna elements are arranged in the y-axis direction, $n_y^2$ sets of time-series data items can be obtained.

Figure 3:
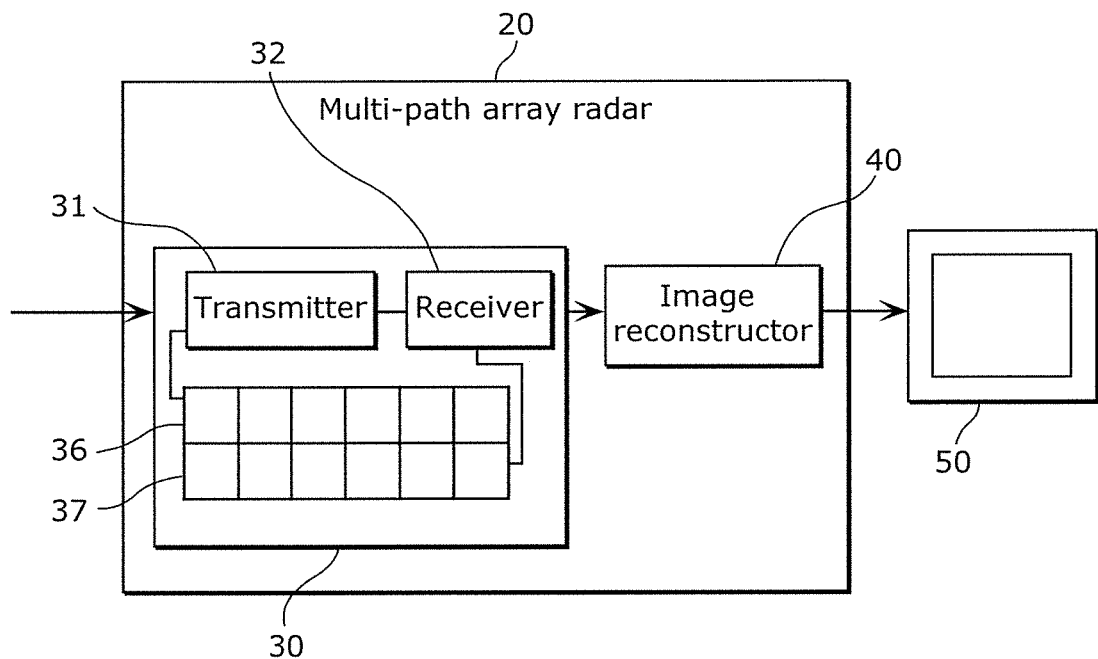
FIG. 3 schematically illustrates a configuration of a multi-path array radar according to Embodiment 1.

FIG. 3 schematically illustrates a configuration of the multi-path array radar 20 according to Embodiment 1. As illustrated in FIG. 3, the multi-path array radar 20 includes a sensor 30 and an image reconstructor 40.

The sensor 30 includes a transmitter 31, a receiver 32, transmitting antenna elements 36, and receiving antenna elements 37.

In the linear array antenna, the transmitting antenna elements 36 are arranged in a straight line, and the receiving antenna elements 37 are arranged in a straight line, as illustrated in FIG. 3. The transmitting antenna elements 36 transmit waves toward an object, and the receiving antenna elements 37 receive reflected waves (scattered waves) that are waves reflected off (scattered by) the object. Although electromagnetic waves are cited in the following descriptions as an example of the above waves, the waves are not limited to electromagnetic waves and may be ultrasonic waves.

The transmitter 31 adjusts (i) the timing of transmitting electromagnetic waves that are to be radiated from the transmitting antenna elements 36, (ii) the number of times the electromagnetic waves are transmitted, and (iii) the transmission gain of the electromagnetic waves.

The receiver 32 conveys to the image reconstructor 40 data of scattered waves of the electromagnetic waves received by the receiving antenna elements 37. At this time, the received data of scattered waves may be amplified or be subjected to signal processing, such as A/D conversion, by the receiver 32.

The image reconstructor 40 analyzes the data of scattered waves conveyed from the receiving unit 32 and visualizes the data of scattered waves using a later-described image reconstruction algorithm. Thus, images according to information on the interior of an object are reproduced on a monitor 50.

When the above-described linear array antenna in the multi-path array radar 20 moves in the x-axis direction, $n_x n_y^2$ sets of time-series data items are obtained. With $n_t$ time series, the number of data items to be obtained is $n_x n_y^2 n_t$ in total. The information quantity of the $n_x n_y^2 n_t$ data items obtained in this way has $n_y$ times greater redundancy than $n_x n_y n_t$ data items necessary for three-dimensional visualization. Therefore, adapting this data to a visualization function in the later-described image reconstruction algorithm allows three-dimensional images according to information on the interior of an object to be reproduced.

Furthermore, the distance between (i) the transmitting antenna elements 36 and (ii) the receiving antenna elements 37 can be freely chosen, meaning that the gain of waves can be changed according to a pair of the transmitting antenna elements 36 and the receiving antenna elements 37 (a path-dependent variable gain amplification function) to change the depth of an object to which the inspection is possible.

Hereinafter, a process flow of visualizing information on the interior of an object according to the scattering tomography method is described.

Process Flow of Scattering Tomography Method

Figure 4:
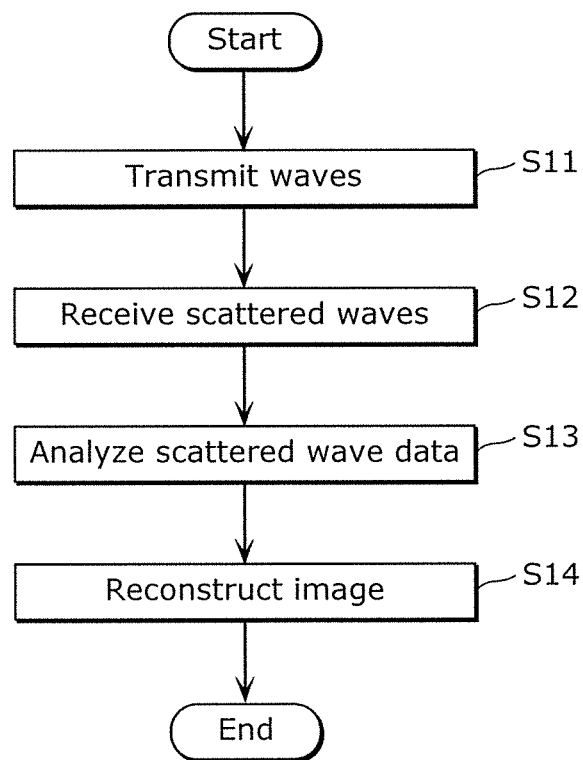
FIG. 4 is a flowchart representing operations of a multi-path array radar according to Embodiment 1.

FIG. 4 is a flowchart representing operations of the multi-path array radar 20 illustrated in FIG. 3.

As illustrated in FIG. 4, a method of visualizing (imaging) information on the interior of an object according to the scattering tomography method is as follows.

First, waves are radiated from the transmitting antenna elements 36 toward tunnel lining concrete that is an object (S11). As the waves, ultrasonic waves are used, for example. The transmitter 31 adjusts the wavelength, the amplitude, and the like of ultrasonic waves, and the transmitting antenna elements 36 radiate the adjusted ultrasonic waves to the concrete.

Next, reflected waves (scattered waves) that have been reflected off a flaw inside the concrete are received by the receiving antenna elements 37 (S12). The received scattered waves may be, for example, amplified or subject to A/D conversion by the receiver 32, that is, may be converted into a type suitable for analysis that is performed by the image reconstructor 40.

Next, scattered wave data representing the received scattered waves are conveyed from the receiver 32 to the image reconstructor 40. The image reconstructor 40 analyzes the conveyed scattered wave data (S13). Herein, the scattered wave data is analyzed using the later-described image reconstruction algorithm. Specifically, a visualization function is derived. With this, images (an image) corresponding to a flaw inside the concrete are reconstructed (S14).

Furthermore, data of the reconstructed images is conveyed from the image reconstructor 40 to the monitor 50 and reproduced on the monitor 50.

Hereinafter, the image reconstruction algorithm that is used by the image reconstructor 40 is described. This image reconstruction algorithm is a principle of the scattering tomography method according to the present invention.

Image Reconstruction Algorithm

Figure 5:
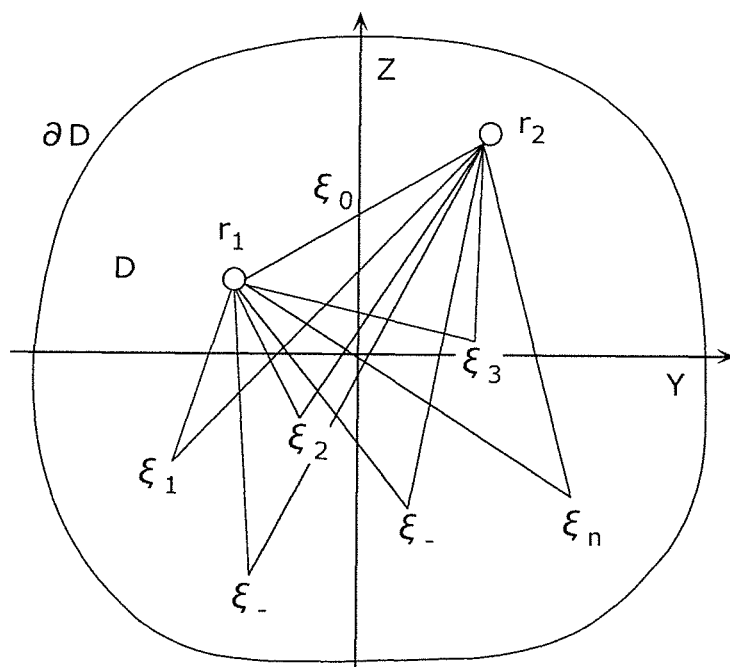
FIG. 5 illustrates an analysis model for explaining a principle of a scattering tomography method according to Embodiment 1.
Figure 6:
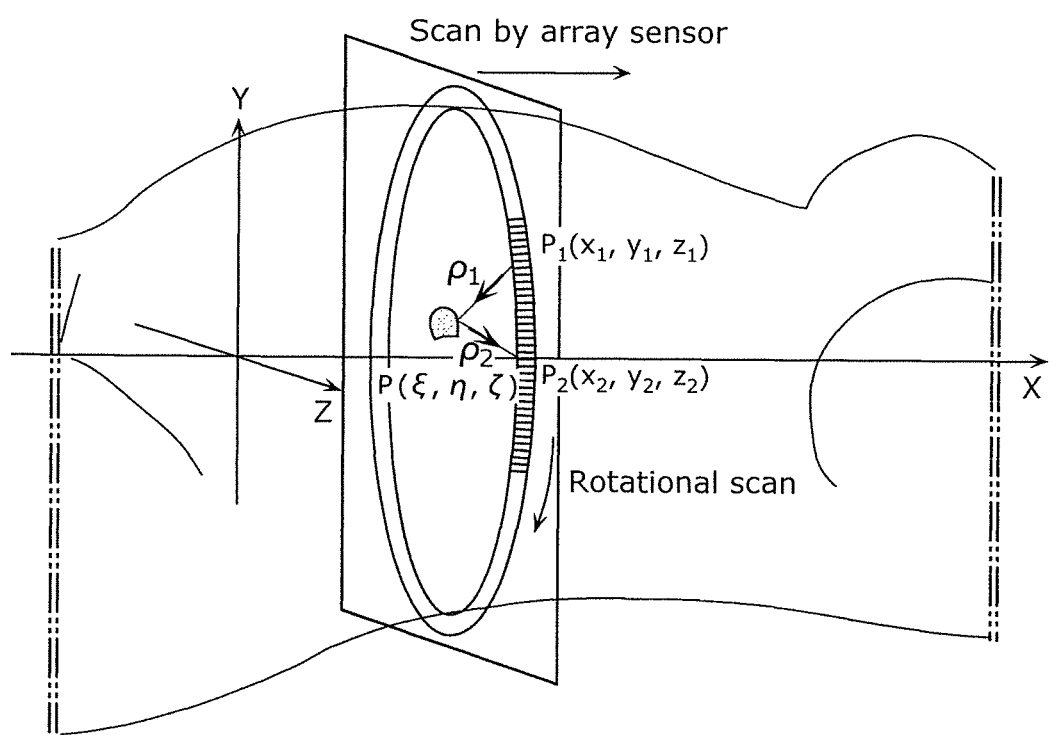
FIG. 6 illustrates an analysis model for explaining a principle of a scattering tomography method according to Embodiment 1.

FIG. 5 and FIG. 6 illustrate an analysis model for explaining a principle of a scattering tomography method according to this embodiment. The following describes derivation of a visualization function that is applied in the case where the sensor 30 is a one-dimensional sensor array, using the model illustrated in FIG. 5 and FIG. 6 as an analysis model.

In the case of the image reconstruction algorithm (theory) described below, wave radiation points (the transmitting antenna elements 36) and wave receiving points (the receiving antenna elements 37) are arranged in a curve in an arbitrary manner, and information on the interior of an object is visualized using transmitted data representing waves radiated from the wave radiation points and scattered wave data representing scattered waves received at the wave receiving points.

As illustrated in FIG. 6, the x-axis direction corresponds to the tunnel depth direction, and a two-dimensional profile that is perpendicular to the x-axis direction and moves along the x-axis direction is defined as a y-z plane. Specifically, in this analysis model, the transmitting antenna elements 36 and the receiving antenna elements 37 are provided in a curve (on a part of the circumference of a circle) on the y-z plane.

A brief mathematical explanation of the image reconstruction algorithm is as follows: a fundamental solution (function) necessary for visualization is set first, an equation is constructed from the solution, and a more general solution is determined using transmitted data and received data, that is, the inverse problem is solved.

More specifically, the Green's function necessary for visualization is set first. A function that becomes a solution of this Green's function is then introduced. A partial differential equation in six-dimensional space (t, x, $y_1$, $y_2$, $z_1$, $z_2$) the exact solution (the function) of which is the above-mentioned function is then constructed. This partial differential equation is then solved using, as a boundary condition, the transmitted data of waves radiated from the transmitting antenna elements 36 arranged in a curve and the received data of waves received by the receiving antenna elements 37 arranged in the curve, and a visualization function is determined where t→0, x→x, $z_2$→$z_1$ (=z), and $y_1$→$y_2$ (=y). Thus, the visualization function is determined, allowing information on the interior of an object, such as a flaw inside concrete, to be visualized in a versatile manner at high speed.

A specific example is as follows.

1. Inverse Problem of Scattering and the Green's Function

Suppose a situation where waves radiated from $r_1$ are reflected off a point ξ and travel to a point $r_2$ as in FIG. 5. Under the condition that a frequency ω is constant, the wave transmitting point $r_1$ and the wave receiving point $r_2$ freely move inside an x cross-section D while the wave transmitting point $r_1$ and the wave receiving point $r_2$ satisfy a certain constraint. Data obtained in this case is denoted by $G(r_1, r_2, \omega)$. This function relates to distribution of reflection points within a region. Herein, ω=2πf where ω represents an angular frequency. $G(r_1, r_2, \omega)$ is a sum of reflected signals from all the points ξ. Since there are many reflection points within the region, $G(r_1, r_2, w)$ can be written as in Expression 1.

[Math. 1]

$$G(r_1,r_2,\omega) = \iiint_D \varphi(r_1 \to \xi \to r_2, \omega) d\xi \qquad \text{Expression 1}$$

In this equation, [Math. 2] represents signal intensity of the waves radiated from the point $r_1$, reflected off the point and traveled to the point $r_2$.

$$\varphi(r_1 \to \xi \to r_2, \omega) \qquad \text{[Math. 2]}$$

The constraint that restricts the wave transmitting point $r_1$ and the wave receiving point $r_2$ is a condition that the x-coordinate of and the x-coordinate of $r_2$ are always equal.

A theoretical structure of the inverse problem of scattering is described using this function $G(r_1, r_2, \omega)$.

A partial region of three-dimensional space is denoted by D, and a boundary of the region is denoted by ∂D. In this case, the function $G(r_1, r_2, w)$ is a solution of a differential equation such as Expression 2 below inside the region D. This equation is called as a scattered field equation.

[Math. 3]

$$L\left(\frac{\partial}{\partial t}, \frac{\partial}{\partial r_1}, \frac{\partial}{\partial r_2}\right)\overline{G}(r_1, r_2, t) = 0 \qquad \text{Expression 2}$$

where $\overline{G}(r_1,r_2,t)$ is a function obtained by the Fourier transform of $G(r_1, r_2, \omega)$ with respect to ω.

The value of $G(r_1, r_2, \omega)$ at the boundary ∂D is a value measured by the sensor 30 (the transmitted data and the received data). The above equation is solved under this boundary condition, and based on the result, ρ(r) is defined as Expression 3 below.

[Math. 4]

$$\rho(r) = \lim_{t \to 0}[Tr[\overline{G}(r_1, r_2, t)]] = \overline{G}(r, r, 0) \qquad \text{Expression 3}$$

Herein, ρ(r) is a function related to a slope of a dielectric constant within the region D that is to be determined. In practice, it is necessary to determine a differential operator $L(\partial/\partial t, \partial/\partial r_1, \partial/\partial r_2)$ expressed above.

Figure 7:
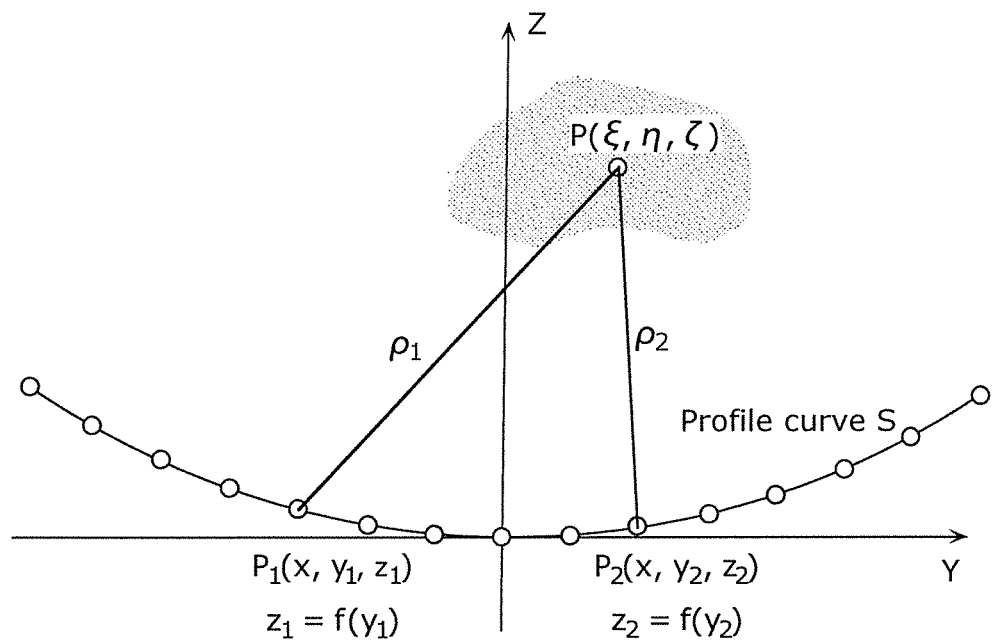
FIG. 7 illustrates an analysis model for explaining a principle of a scattering tomography method according to Embodiment 1.
Figure 8:
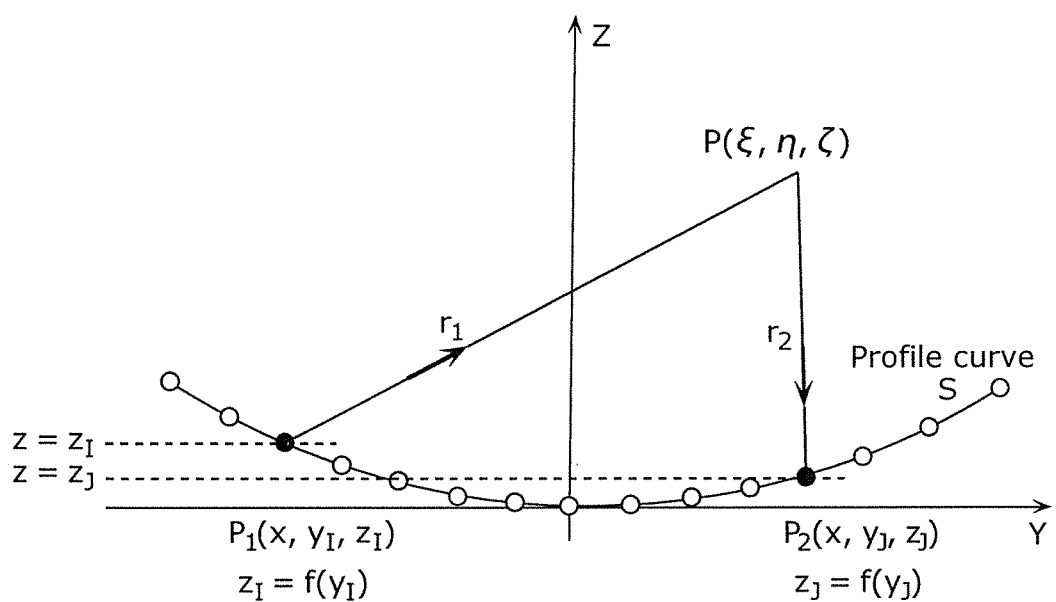
FIG. 8 illustrates an analysis model for explaining a principle of a scattering tomography method according to Embodiment 1.

2. Derivation of Inverse Problem $L(\partial/\partial t, \partial/\partial r_1, \partial/\partial r_2)$ of Scattering in Arbitrary Curved Surface Next, a method of determining the above-described differential operator is described. FIG. 6 to FIG. 8 illustrate an analysis model for explaining the method of determining the differential operator.

Using a one-dimensional sensor array illustrated in FIG. 6, suppose that the one-dimensional sensor array moves in the x-axis direction while performing a rotational scan. FIG. 7 and FIG. 8 are enlarged views of a part of the sensor array illustrated in FIG. 6.

As illustrated in FIG. 7 and FIG. 8, waves radiated from a point $P_1$ are reflected off a point P and travel to a point $P_2$. In addition, assume that a measurement point moves on a profile curve S.

The y-z coordinates of $r_1$ and $r_2$ on an arbitrary curve are expressed as $r_1=(x, y_1, z_1)$ and $r_2=y_2, z_2)$. In this case, the function G is defined as Expression 4 below.

[Math. 5]

$$G(r_1,r_2,\omega)\iiint_D \varphi(r_1 \to \xi \to r_2\omega)d\xi \quad \text{Expression 4}$$

Next, a function $\phi$ such as Expression 5 below is introduced. In this case, the following relationships hold: $\omega=ck$ and $k=2\pi/\lambda$ where c is a speed of propagation; k is wave number; and $\lambda$ is a wavelength. In Expression 5: $\phi$ corresponds to a function (a solution) for reconstructing an image relating to information on the interior of an object according to the present invention, that is, a function defined in Expression A according to the present invention; and $\xi$, $\eta$, and $\zeta$ are the x-coordinate, the y-coordinate, and z-coordinate, respectively, of the point P ($\xi$, $\eta$, $\zeta$) illustrated in FIG. 6 to FIG. 8. The point P ($\xi$, $\eta$, $\zeta$) is an arbitrary scattering point within the region.

[Math. 6]

$$\phi(x, y_1, y_2, z_1, z_2, \omega) = \int\int_D \frac{e^{ik\rho_1}}{\rho_1}\frac{e^{ik\rho_2}}{\rho_2}\varepsilon(\xi, \eta, \zeta)d\xi d\eta d\zeta \quad \text{Expression 5}$$

$$\rho_1 = \sqrt{(x-\xi)^2 + (y_1-\eta)^2 + (z_1-\zeta)^2}$$

$$\rho_2 = \sqrt{(x-\xi)^2 + (y_2-\eta)^2 + (z_2-\zeta)^2}$$

Herein, it is assumed that a time factor is proportional to $\exp(-i\omega t)$, and wave number is denoted by k. The function in the term to be integrated in the above expression is [Math. 7] in Expression 4 and represented as Expression 6 below.

[Math. 7]

$$\varphi$$

[Math. 8]

$$\varphi = \frac{e^{ik\rho_1}}{\rho_1}\frac{e^{ik\rho_2}}{\rho_2}\varepsilon(\xi, \eta, \zeta) \quad \text{Expression 6}$$

Next, a partial differential equation the asymptotic solution (the function) of which is Expression 5 is determined. In order for this to be done, high-order terms are ignored in calculation for $1/\rho$ resulting from differentiation. Hereinafter, an abridged notation for differentiation is defined as Expression 7 below.

[Math. 9]

$$\frac{\partial}{\partial t} \to \partial_t, \frac{\partial}{\partial x} \to \partial_x, \frac{\partial}{\partial y_1} \to \partial_{y_1},$$

$$\frac{\partial}{\partial y_2} \to \partial_{y_2}, \frac{\partial}{\partial z_1} \to \partial_{z_1}, \frac{\partial}{\partial z_2} \to \partial_{z_2} \quad \text{Expression 7}$$

With this, $\phi$ satisfies the equation represented in Expression 8 below. This Expression 8 corresponds to the scattered field equation according to the present invention.

[Math. 10]

$$\left[\frac{1}{4}\Delta_5^2 - (ik)^2\partial_x^2 - (\partial_{y_1}^2 + \partial_{z_1}^2)(\partial_{y_2}^2 + \partial_{z_2}^2)\right]\phi = 0 \quad \text{Expression 8}$$

where $$\Delta_5 = \partial_x^2 + \partial_{y_1}^2 + \partial_{y_2}^2 + \partial_{z_1}^2 + \partial_{z_2}^2$$

Although a steady-state case is assumed in derivation of Expression 8, it is easy to extend Expression 8 to an unsteady-state case. For this purpose, a replacement of a variable such as Expression 9 below is performed.

[Math. 11]

$$-ik \to \frac{1}{c}\partial_t \quad \text{Expression 9}$$

This leads to Expression 10 below lastly. This Expression 10 corresponds to the equation defined in Expression B according to the present invention.

[Math. 12]

$$\left[\frac{1}{4}\Delta_5^2 - \frac{1}{c^2}\partial_t^2\partial_x^2 - (\partial_{y_1}^2 + \partial_{z_1}^2)(\partial_{y_2}^2 + \partial_{z_2}^2)\right]\phi = 0 \quad \text{Expression 10}$$

Next, a solution of Expression 10 is determined assuming that a time factor of $\phi$ is proportional to $\exp(-i\omega t)$. First, the multi-dimensional Fourier transform of $\phi$ in Expression 10 with respect to t, x, $y_1$, and $y_2$ results in Expression 11 below.

[Math. 13]

$$\tilde{\phi}(k_x, k_{y_1}, k_{y_2}, z_1, z_2, \omega) = \int_{-\infty}^{\infty}e^{i\omega t}dt \int_{-\infty}^{\infty}e^{ik_{y_1}y_1}dy_1 \quad \text{Expression 11}$$

$$\int_{-\infty}^{\infty}e^{ik_{y_2}y_2}dy_2 \int_{-\infty}^{\infty}e^{ik_x x}\phi(x, y_1, y_2, z_1, z_2, t)dx$$

Note that the use of a fast Fourier transform makes it possible to obtain analysis data at high speed. Thus, analysis time can be shortened.

Assuming that partial differentials of $z_1$ and $z_2$ are $Dz_1$ and $Dz_2$, respectively, Expression 12 below is obtained.

[Math. 14]

$$\{(D_{z_1}^2+D_{z_2}^2-k_x^2-k_{y_1}^2-k_{y_2}^2)^2-4k^2k_x^2-4(D_{z_1}^2-k_{y_1}^2)(D_{z_2}^2-k_{y_2}^2)\}\tilde{\phi}=0 \quad \text{Expression 12}$$

This equation, which is to be solved, has two variables $z_1$ and $z_2$. Therefore, in order to solve Expression 12, a boundary condition for fixed (x, $y_1$, $y_2$) or ($k_x$, $k_{y1}$, $k_{y2}$) is necessary which is given in a one-dimensional region within ($z_1$, $z_2$) space.

However, the boundary condition obtained by the measurement with the radar is that only given at one point (f($y_1$), f($y_2$)) within the ($z_1$, $z_2$) space.

Therefore, in order to solve this problem, consistency is required between the present theory and the theory held in the case where $z_1=z$ and $z_2=z$. Specifically, the present theory in which $z_1$ and $z_2$ are independent is required to include special solutions $z_1=z$ and $z_2=z$.

Assume that a solution of Expression 12 is Expression 13 below.

[Math. 15]

$$E(k_x, k_{y_1}, k_{y_2}, z_1, z_2) = \exp(is_1 z_1)\exp(is_2 z_2) \quad \text{Expression 13}$$

When $z_1=z_2=z$, Expression 13 becomes Expression 14 below.

[Math. 16]

$$E(k_x, k_{y_1}, k_{y_2}, z_1, z_2) = \exp\{i(s_1+s_2)z\} \quad \text{Expression 14}$$

When Expression 13 is substituted for Expression 12, Expression 15 below is obtained. This Expression 15 is one boundary condition.

[Math. 17]

$$(s_1^2 + s_2^2 + k_x^2 + k_{y_1}^2 + k_{y_2}^2)^2 - 4k^2 k_x^2 - 4(s_1^2 + k_{y_1}^2)(s_2^2 + k_{y_2}^2) = 0 \quad \text{Expression 15}$$

Furthermore, another equation is necessary as the boundary condition. Here, Expression 16 below is derived from the above-mentioned consistency requirement.

[Math. 18]

$$s_1 + s_2 = \sqrt{\left(\sqrt{k^2 - k_{y_1}^2} + \sqrt{k^2 - k_{y_2}^2}\right)^2 - k_x^2} \quad \text{Expression 16}$$

Using Expression 15 and Expression 16, $s_1(k_x, k_{y1}, k_{y2})$ and $s_2(k_x, k_{y1}, k_{y2})$ are determined to be those represented in Expression 17 below.

[Math. 19]

$$s_1(k_x, k_{y_1}, k_{y_2}) = \quad \text{Expression 17}$$

$$\frac{\sqrt{k^2 - k_{y_1}^2}\sqrt{\left(\sqrt{k^2 - k_{y_1}^2} + \sqrt{k^2 - k_{y_2}^2}\right)^2 - k_x^2}}{\sqrt{k^2 - k_{y_1}^2} + \sqrt{k^2 - k_{y_2}^2}}$$

$$s_2(k_x, k_{y_1}, k_{y_2}) =$$

$$\frac{\sqrt{k^2 - k_{y_2}^2}\sqrt{\left(\sqrt{k^2 - k_{y_1}^2} + \sqrt{k^2 - k_{y_2}^2}\right)^2 - k_x^2}}{\sqrt{k^2 - k_{y_1}^2} + \sqrt{k^2 - k_{y_2}^2}}$$

A specific process of the calculation is performed later. A solution of the equation in Expression 13 can be written as Expression 18 below using these $s_1(k_x, k_{y1}, k_{y2})$ and $s_2(k_x, k_{y1}, k_{y2})$.

[Math. 20]

$$\phi(x, y_1, y_2, z_1, z_2, k) = \quad \text{Expression 18}$$

$$\frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a(k_x, k_{y_1}, k_{y_2})$$

$$e^{is_1(k_x, k_{y_1}, k_{y_2})z_1} e^{is_2(k_x, k_{y_1}, k_{y_2})z_2} dk_x dk_{y_1} dk_{y_2}$$

Here, assume that an equation of the profile curve S with x fixed is, for example, Expression 19 below. Although this is not an essential assumption, assume a paraboloid, for example.

[Math. 21]

$$f(y) = \alpha y^2 \quad \text{Expression 19}$$

In this case, the boundary condition given on the profile curve S is Expression 20 below.

[Math. 22]

$$\phi(x, y_1, y_2, \alpha y_1^2, \alpha y_2^2, k) = \quad \text{Expression 20}$$

$$\frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a(k_x, k_{y_1}, k_{y_2})$$

$$e^{i\alpha\{s_1(k_x, k_{y_1}, k_{y_2})y_1^2 + s_2(k_x, k_{y_1}, k_{y_2})y_2^2\}} dk_x dk_{y_1} dk_{y_2}$$

This equation is used to determine $a(k_x, k_{y1}, k_{y2})$. Here, the abridged notations indicated in Expression 21 below are used.

[Math. 23]

$$a(k) = a(k_x, k_{y_1}, k_{y_2})$$

$$s_1(k) = s_1(k_x, k_{y_1}, k_{y_2})$$

$$s_2(k) = s_2(k_x, k_{y_1}, k_{y_2}) \quad \text{Expression 21}$$

Using the abridged notations indicated in Expression 21, Expression 20 becomes an integral equation with respect to $a(k_x, k_{y1}, k_{y2})$ indicated in Expression 22 below.

[Math. 24]

$$\phi(x, y_1, y_2, \alpha y_1^2, \alpha y_2^2, k) = \quad \text{Expression 22}$$

$$\frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)}$$

$$a(k) e^{i\alpha\{s_1(k)y_1^2 + s_2(k)y_2^2\}} dk$$

If a(k) can be determined from this expression, a solution of the equation of Expression 8 is represented as Expression 23 below based on Expression 18.

[Math. 25]

$$\phi(x, y_1, y_2, z_1, z_2, k) = \frac{1}{(2\pi)^3} \quad \text{Expression 23}$$

$$\int_{-\infty}^{\infty}\int_{-\infty}^{\infty}\int_{-\infty}^{\infty} e^{-i(k_x x + k_{y_1} y_1 + k_{y_2} y_2)} a(k) e^{is_1(k)z_1} e^{is_2(k)z_2} dk$$

The Fourier transform of Expression 23 with respect to k where $z_1=z_2=z$ results in a function represented in Expression 24 below. This Expression 24 corresponds to a visualization function defined in Expression C according to the present invention.

[Math. 26]

$$\rho(r) = \lim_{t \to 0} \left[ \frac{1}{2\pi} \int_{-\infty}^{\infty} \phi(x, y, y, z, z, k) e^{-ickt} dk \right] \quad \text{Expression 24}$$

Thus, a final visualization function $\rho(r)$ is obtained.

3. Solution of Integral Equation (Expression 22)

Next, a solution of the above-mentioned Expression 22 is determined. Specifically, as illustrated in FIG. 8, approximate data in the xy plane (the plane z=0) is determined from data measured at points $P_I$ and $P_J$ on the profile curve S.

With respect to $\phi$ in Expression 22, data $\phi(x, y_I, y_J, z_U, z_J, t)$ measured at the points $P_I$ and $P_J$ on the curve is Fourier transformed, and assume that resultant $\Phi(k_x, y_I, y_J, k)$ is Expression 25 below.

[Math. 27]

$$\Phi_{I,J}(k_x, y_I, y_J, k) = \int_{-\infty}^{\infty} \int_{-\infty}^{\infty} e^{-ikt - ik_x x} \phi(x, y_I, y_J, z_I, z_J, t) dt dx \quad \text{Expression 25}$$

Since $z_I$ and $z_J$ are on the profile curve as illustrated in FIG. 8, Expression 26 below holds.

[Math. 28]

$$z_I = f(y_I)$$

$$z_J = f(y_J) \quad \text{Expression 26}$$

Furthermore, Expression 27 below is obtained from Expression 18.

[Math. 29]

$$\Phi(k_x, y_I, y_J, k) = \quad \text{Expression 27}$$
$$\frac{1}{(2\pi)^2} \int_{-\infty}^{\infty} \int_{-\infty}^{\infty} e^{-i(k_{y_1} y_I + k_{y_2} y_J)} a_{I,J}(k_x, k_{y_1}, k_{y_2}, k)$$
$$e^{is_1(k, k_x, k_{y_1}, k_{y_2})z_I} e^{is_2(k, k_x, k_{y_1}, k_{y_2})z_J} dk_{y_1} dk_{y_2}$$

This Expression 27 can be written as Expression 28 below by way of interpretation.

[Math. 30]

$$\Phi(k_x, y_I, y_J, k) \delta(y_1 - y_I) \delta(y_2 - y_J) = \quad \text{Expression 28}$$
$$\frac{1}{(2\pi)^2} \int_{-\infty}^{\infty} \int_{-\infty}^{\infty} e^{-i(k_{y_1} y_1 + k_{y_2} y_2)} a_{I,J}(k_x, k_{y_1}, k_{y_2}, k)$$
$$e^{is_1(k, k_x, k_{y_1}, k_{y_2})z_I} e^{is_2(k, k_x, k_{y_1}, k_{y_2})z_J} dk_{y_1} dk_{y_2}$$

When both sides of Expression 28 are Fourier transformed, Expression 29 below is obtained.

[Math. 31]

$$\int_{-\infty}^{\infty} \int_{-\infty}^{\infty} e^{i(k'_{y_1} y_1 + k'_{y_2} y_2)} \quad \text{Expression 29}$$
$$\Phi(k_x, y_I, y_J, k) \delta(y_1 - y_I) \delta(y_2 - y_J) dy_1 dy_2 =$$
$$\int_{-\infty}^{\infty} \int_{-\infty}^{\infty} e^{i(k'_{y_1} y_1 + k'_{y_2} y_2)} \left\{ \frac{1}{(2\pi)^2} \int_{-\infty}^{\infty} \int_{-\infty}^{\infty} e^{-i(k_{y_1} y_1 + k_{y_2} y_2)} \right.$$
$$a_{I,J}(k_x, k_{y_1}, k_{y_2}, k) e^{is_1(k, k_x, k_{y_1}, k_{y_2})z_I}$$
$$\left. e^{is_2(k, k_x, k_{y_1}, k_{y_2})z_J} dk_{y_1} k_{y_2} \right\} dy_1 dy_2$$

When both sides of Expression 29 are integrated, the following holds.

[Math. 32]

Expression 30

$$e^{i(k'_{y_1} y_I + k'_{y_2} y_J)} \Phi(k, k_x, y_I, y_J) = \left\{ \int_{-\infty}^{\infty} \int_{-\infty}^{\infty} \delta(k_{y_1} - k'_{y_1}) \delta(k_{y_2} - k'_{y_2}) a(k_x, k_{y_1}, k_{y_2}, k) e^{is_1(k, k_x, k_{y_1}, k_{y_2})z_I} e^{is_2(k, k_x, k_{y_1}, k_{y_2})z_J} dk_{y_1} k_{y_2} \right\}$$
$$= a_{I,J}(k_x, k'_{y_1}, k'_{y_2}, k) e^{is_1(k, k_x, k'_{y_1}, k'_{y_2})z_I} e^{is_2(k, k_x, k'_{y_1}, k'_{y_2})z_J}$$

In this way, $a_{I,J}$ is obtained as in Expression 31 below.

[Math. 33]

$$a_{I,J}(k_x, k_{y_1}, k_{y_2}, k) = e^{i(k_{y_1} y_I + k_{y_2} y_J)} e^{-is_1(k, k_x, k_{y_1}, k_{y_2})z_I} e^{-is_2(k, k_x, k_{y_1}, k_{y_2})z_J} \Phi(k_x, y_I, y_J, k) \quad \text{Expression 31}$$

When a sum of all values for I and J is obtained, Expression 32 below is obtained.

[Math. 34]

Expression 32

$$a(k_x, k_{y_1}, k_{y_2}, k) = \sum_{I,J} a_{I,J}(k_x, k_{y_1}, k_{y_2}, k)$$
$$= \sum_{I,J} e^{i(k_{y_1} y_I + k_{y_2} y_J)} e^{-is_1(k, k_x, k_{y_1}, k_{y_2})z_I} e^{-is_2(k, k_x, k_{y_1}, k_{y_2})z_J} \Phi(k_x, y_I, y_J, k)$$

In this way, conversion into a boundary condition in the plane z=0 can be achieved.

When a solution of the partial differential equation in Expression 10 is obtained using the boundary condition where z=0, Expression 33 below is obtained from Expression 18.

[Math. 35]

$$\phi(x, y_1, y_2, z_1, z_2, k) = \frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a(k_x, k_{y_1}, k_{y_2}, k) e^{is_1(k_x, k_{y_1}, k_{y_2})z_1} e^{is_2(k_x, k_{y_1}, k_{y_2})z_2} dk_x dk_{y_1} dk_{y_2}$$

Expression 33

At this time, the visualization function for reconstructing an image is obtained by integrating Expression 34 for k.

[Math. 36]

$$\phi(x, y, y, z, k) = \lim_{y_1 \to y}[\phi(x, y_1, y, z, k)] =$$

$$\lim_{y_1 \to y}\left[\frac{1}{(2\pi)^3}\int_{-\infty}^{\infty}\int_{-\infty}^{\infty}\int_{-\infty}^{\infty} e^{-i(k_x x + k_{y_1} y_1 + k_y y)} a(k, k_x, k_{y_1}, k_y, k) e^{i\left\{\sqrt{\left(\sqrt{k^2 - k_{y_1}^2} + \sqrt{k^2 - k_y^2}\right)^2 - k_x^2}\right\}z} dk_x dk_{y_1} dk_y\right]$$

Expression 34

Upon integrating Expression 34 for k, a variable $k_z$ represented as follows is introduced. In Expression 35, an expression of k using $k_z$ and a function obtained by differentiating the expression of k are shown.

[Math. 37]

$$k_z = \sqrt{\left(\sqrt{k^2 - k_{y_1}^2} + \sqrt{k^2 - k_{y_1}^2}\right)^2 - k_x^2}$$

$$k = \frac{1}{2}\sqrt{k_x^2 + k_z^2 + \frac{(k_{y_1}^2 - k_{y_2}^2)^2}{k_x^2 + k_z^2} + 2(k_{y_1}^2 + k_{y_2}^2)}$$

$$\frac{dk}{dk_z} = \frac{k_z\sqrt{k^2 - k_{y_1}^2}\sqrt{k^2 - k_{y_1}^2}}{k(k_x^2 + k_z^2)}$$

Expression 35

In this way, the visualization function ρ(x, y, z) for reconstructing an image is lastly represented as Expression 36 below.

[Math. 38]

$$\rho(x, y, z) = \int_{-\infty}^{\infty} \phi(x, y, y, z, k) dk$$

$$= \int_{-\infty}^{\infty} \lim_{y_1 \to y}[\phi(x, y_1, y, z, k)] dk$$

$$= \int_{-\infty}^{\infty} \lim_{y_1 \to y}\left[\frac{1}{(2\pi)^3}\int_{-\infty}^{\infty}\int_{-\infty}^{\infty}\int_{-\infty}^{\infty} e^{-i(k_x x + k_{y_1} y_1 + k_y y)} a(k, k_x, k_{y_1}, k_y, k) e^{i\left\{\sqrt{\left(\sqrt{k^2 - k_{y_1}^2} + \sqrt{k^2 - k_y^2}\right)^2 - k_x^2}\right\}z} dk_x dk_{y_1} dk_y\right] dk$$

$$= \int_{-\infty}^{\infty} \lim_{y_1 \to y}\left[\frac{1}{(2\pi)^3}\int_{-\infty}^{\infty}\int_{-\infty}^{\infty}\int_{-\infty}^{\infty} e^{-i(k_x x + k_{y_1} y_1 + k_y y)} e^{ik_z z} a(k, k_x, k_{y_1}, k_y, k)\left(\frac{dk}{dk_z}\right) dk_x dk_{y_1} dk_y dk_z\right]$$

Expression 36

With this visualization function, an image relating to information on the interior of an object is reconstructed. Thus, an image relating to information on the interior of an object, such as a flaw inside concrete, can be visualized in a versatile manner at high speed.

Reconstructed Image Obtained by Scattering Tomography Method

Next, a reconstructed image obtained by the above-described scattering tomography method is described. The following describes a reconstructed image obtained by using, as an analysis model, the model illustrated in FIG. 9.

Figure 9:
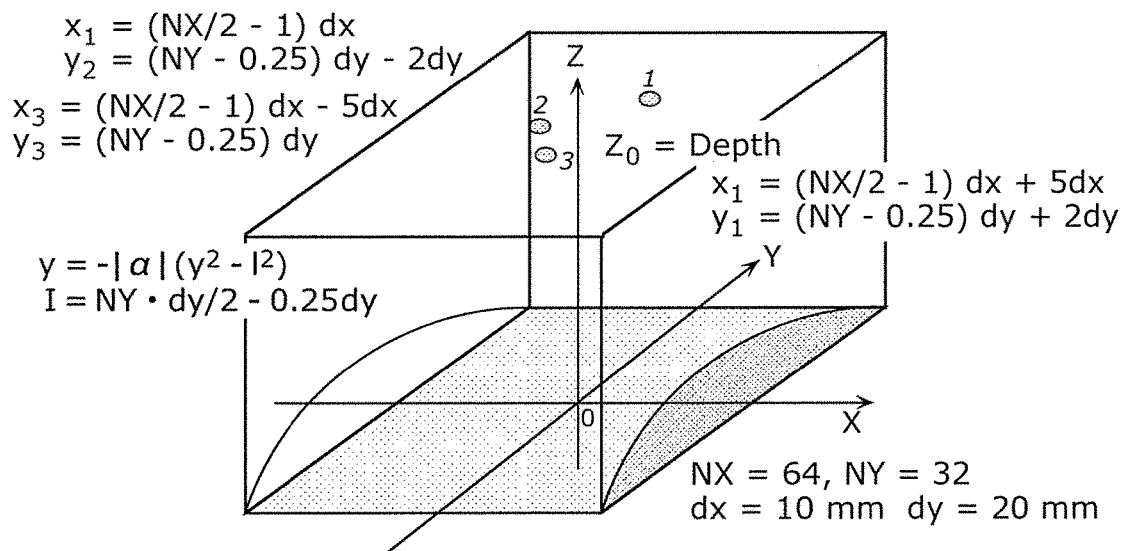
FIG. 9 illustrates an example of an analysis model for analysis using a scattering tomography method according to Embodiment 1.
Figure 10A:
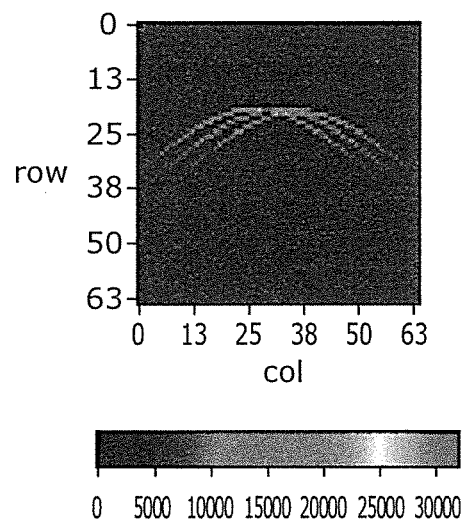
FIG. 10A illustrates scattered wave data obtained in the analysis model illustrated in FIG. 9.
Figure 10B:
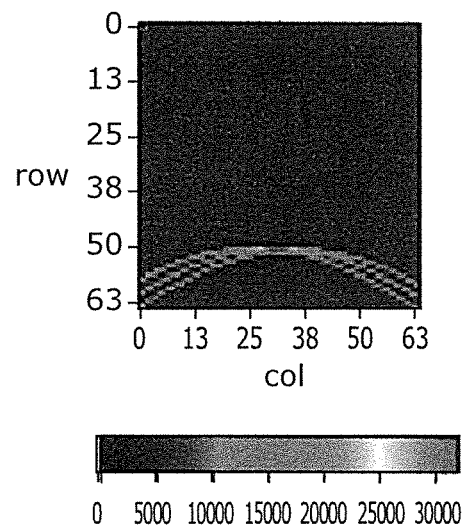
FIG. 10B illustrates scattered wave data obtained in the analysis model illustrated in FIG. 9.

FIG. 9 illustrates an analysis model according to this embodiment. FIG. 10A and FIG. 10B are B-mode images that show raw data as it is, in which dotted reflectors are spread in the form of a hyperbolic curve. FIG. 11A to FIG. 13B illustrate the results of analysis using an existing MPLA radar and the results of analysis using an MPCLA radar according to this embodiment.

In the analysis model illustrated in FIG. 9, an object is a tunnel that has three point flaws in the plane defined at a depth of $Z=Z_0$, and a one-dimensional sensor array detects these point flaws. In FIG. 9, Curvfactor is defined as Curvfactor=N*L/(2R) when it is assumed that the sensor array 10 is arranged on a parabola. In this model, N represents the number of y-axis sensors (N=NY), L represents a total length of the sensor array (L=N*dy), R represents a radius of curvature of the sensor array, dx represents an x-axis scanning pitch, and dy represents a y-axis sensor to sensor distance.

In the results of analysis illustrated in FIG. 10A and FIG. 10B, Curvfactor of an object, i.e., the tunnel, is set to 4.68, and B-mode images are shown; that is, the intensity of scattered waves received by the receiving antenna elements 37 is shown in the form of figures corresponding to a cross-sectional view of the tunnel. Scattered waves received in FIG. 10A are waves scattered when the depth of scatterers is 200 mm, that is, when three flaws are located 200 mm deeper than the surface of the tunnel on which the receiving antenna elements 37 are arranged. Scattered waves received in FIG. 10B are waves scattered when the depth of scatterers is 500 mm, that is, when three flaws are located 500 mm deeper than the surface of the tunnel on which the receiving antenna elements 37 are arranged.

Figure 11A:
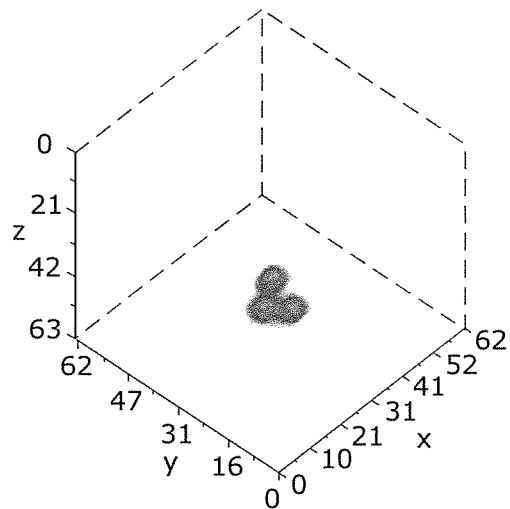
FIG. 11A illustrates observed data obtained by an MPLA radar when curvfactor is 0 in the analysis model illustrated in FIG. 9.
Figure 11B:
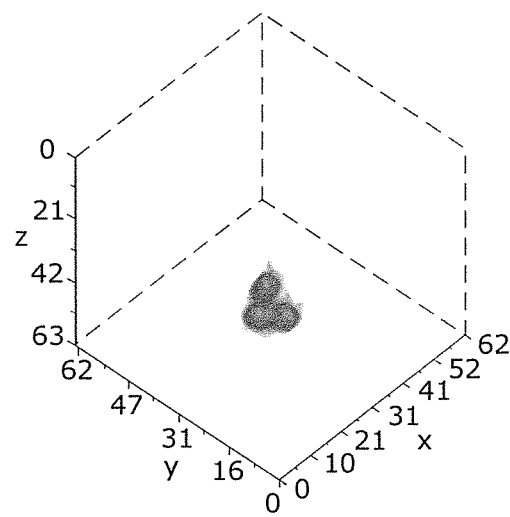
FIG. 11B illustrates observed data obtained by an MPCLA radar when curvfactor is 0 in the analysis model illustrated in FIG. 9.

FIG. 11A and FIG. 11B illustrate the result of analysis using the MPLA radar and the result of analysis using the MPCLA radar, respectively, obtained when curvfactor is 0 (plane) and the depth of scatterers is 500 mm. FIG. 11A and FIG. 11B show that three flaws are measured in the analysis using either method and that the result of the analysis using the MPLA radar and the result of the analysis using the MPCLA radar are not very different from each other.

Figure 12A:
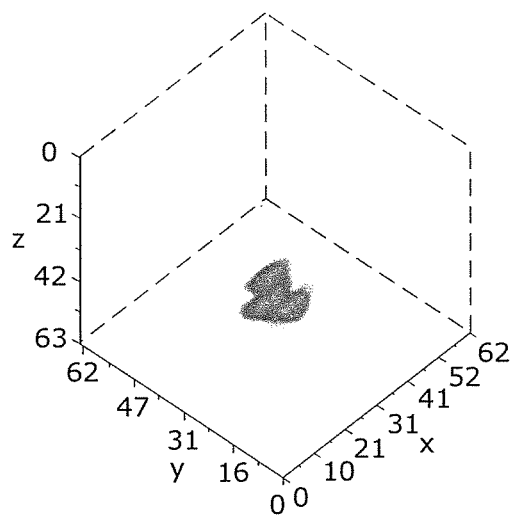
FIG. 12A illustrates observed data obtained by an MPLA radar when curvfactor is 7.02 in the analysis model illustrated in FIG. 9.
Figure 12B:
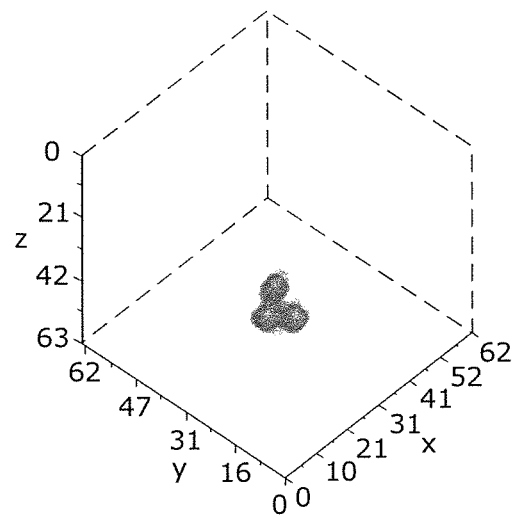
FIG. 12B illustrates observed data obtained by an MPCLA radar when curvfactor is 7.02 in the analysis model illustrated in FIG. 9

FIG. 12A and FIG. 12B illustrate the result of analysis using the MPLA radar and the result of analysis using the MPCLA radar, respectively, obtained when curvfactor is 7.02 and the depth of scatterers is 500 mm. FIG. 12A and FIG. 12B show that three flaws are measured in the analysis using either method, but an image in the result of the analysis using the MPLA radar illustrated in FIG. 12A is out of focus and slightly unclear. In contrast, the result of the analysis using the MPCLA radar illustrated in FIG. 12B shows a clear image of measured three flaws.

Figure 13A:
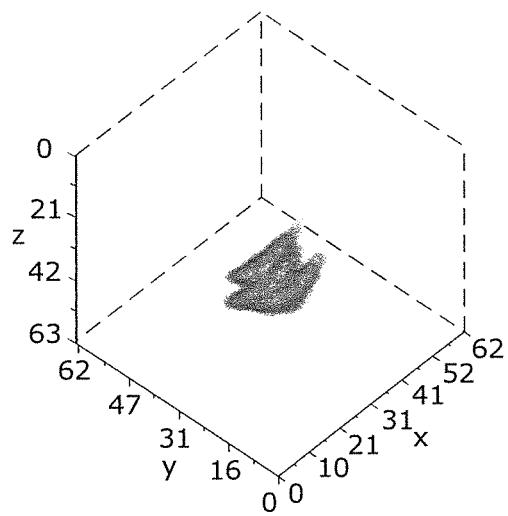
FIG. 13A illustrates observed data obtained by an MPLA radar when curvfactor is 14.04 in the analysis model illustrated in FIG. 9.
Figure 13B:
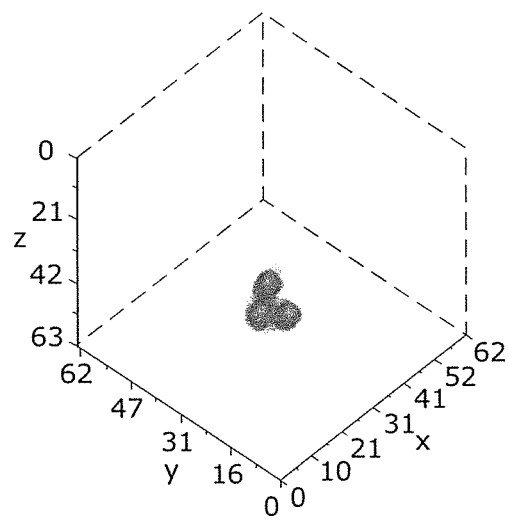
FIG. 13B illustrates observed data obtained by an MPCLA radar when curvfactor is 14.04 in the analysis model illustrated in FIG. 9.

FIG. 13A and FIG. 13B illustrate the result of analysis using the MPLA radar and the result of analysis using the MPCLA radar, respectively, obtained when curvfactor is 14.04 and the depth of scatterers is 500 mm. FIG. 13A and FIG. 13B show that three flaws are measured in the analysis using either method, but an image in the result of the analysis using the MPLA radar illustrated in FIG. 13A is out of focus and unclear. In contrast, the result of the analysis using the MPCLA radar illustrated in FIG. 13B shows a clear image of measured three flaws.

As described above, in the scattering tomography method according to this embodiment, a partial differential equation for the inverse problem is set in an analysis model in which sensor elements are arranged in a curve, and this partial differential equation is solved to obtain a visualization function. Thus, in the scattering tomography method for analyzing scattered waves of waves radiated to an object, information on the interior of an object having a curved surface with high curvature can be visualized in a versatile manner at high speed.

When the above-described linear array antenna in the multi-path array radar 20 moves in the x-axis direction, $n_x n_y^2$ sets of time-series data items are obtained. With $n_t$ time series, the number of data items to be obtained is $n_x n_y^2 n_t$ in total. The information quantity of the $n_x n_y^2 n_t$ data items obtained in this way has $n_y$ times greater redundancy than $n_x n_y n_t$ data items necessary for three-dimensional visualization. Since measurement data has high redundancy as just mentioned, output of the multi-path array radar 20 has high resistance to noise.

Note that the above arithmetic expressions and process flow of deriving the arithmetic expressions are one example; other arithmetic expressions and other deriving process flow may be used.

Although the electromagnetic waves are used as the waves in this embodiment, the electromagnetic waves may be rearranged by ultrasonic waves or the like; Furthermore, although periodic waves having a predetermined frequency are used in this embodiment because the electromagnetic waves are used, the waves may be pulsed waves or the like instead of the periodic waves.

Furthermore, although the tunnel lining concrete is cited as an example of an object in this embodiment, the object is not limited to the tunnel lining concrete and may be other object.

Embodiment 2

Next, Embodiment 2 in the present invention is described.

Embodiment 2 is described in which a two-dimensional sensor array is used as a sensor for performing the scattering tomography method. The two-dimensional sensor array includes a transmitting antenna element and a receiving antenna element arranged in two dimensions on a curved surface (a multi-array antenna).

The configuration of a multi-path array radar serving as a scattering tomography device according to this embodiment is almost the same as that of the multi-path array radar 20 according to Embodiment 1, and is different from that of the multi-path array radar 20 according to Embodiment 1 in that transmitting antenna elements and receiving antenna elements are arranged in two dimensions on a curved surface. Accordingly, an image reconstruction algorithm used by an image reconstructor in the multi-path array radar according to this embodiment is different from that used by the multi-path array radar 20 according to Embodiment Hereinafter, the image reconstruction algorithm in the scattering tomography method according to this embodiment is described.

Image Reconstruction Algorithm

Figure 14:
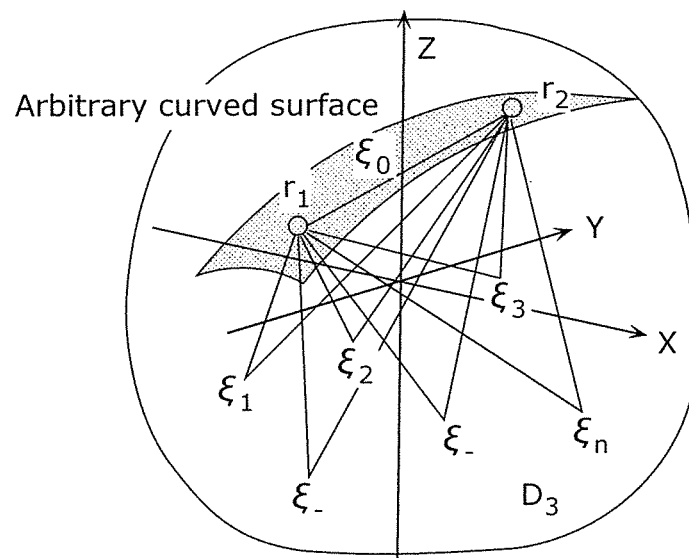
FIG. 14 is an analysis model for explaining a principle of a scattering tomography method according to Embodiment 2.
Figure 15:
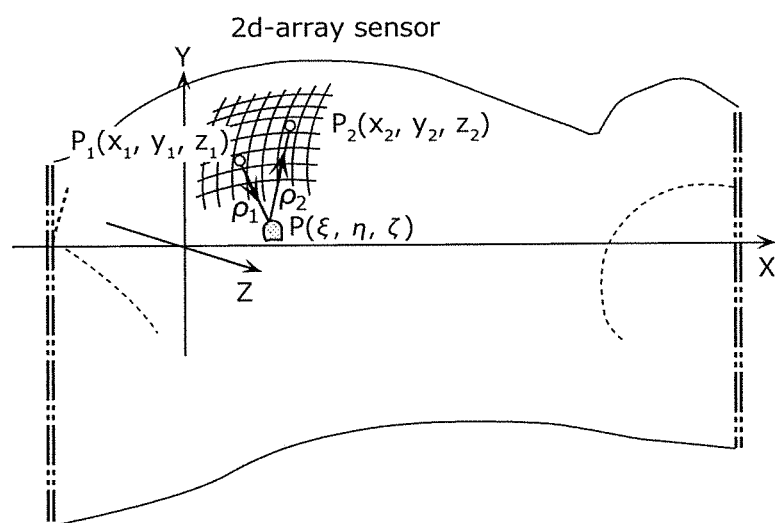
FIG. 15 is an analysis model for explaining a principle of a scattering tomography method according to Embodiment 2.

FIG. 14 and FIG. 15 illustrate an analysis model for explaining a principle of a scattering tomography method according to this embodiment. The following describes derivation of a visualization function that is applied in the case where the model illustrated in FIG. 14 and FIG. 15 is used as an analysis model and the sensor of the multi-path array radar is a two-dimensional sensor array.

In the case of the image reconstruction algorithm (theory) described below, a wave radiation point (one transmitting antenna element 36) and a wave receiving point (one receiving antenna element 37) are arranged on a curved surface in an arbitrary manner, and information on the interior of an object is visualized using transmitted data representing waves radiated from the wave radiation point and scattered wave data representing scattered waves received at the wave receiving point.

FIG. 15 schematically illustrates a two-dimensional sensor array. As illustrated in FIG. 15, x- and y-coordinates are on a surface of the object, and z-coordinates are along a normal of the surface of the object. In this analysis model, the transmitting antenna elements 36 and the receiving antenna elements 37 are provided on a curved surface in xyz-space.

A brief mathematical explanation of the image reconstruction algorithm is, as in the scattering tomography method according to Embodiment 1, as follows: a fundamental solution (function) necessary for visualization is set first, an equation is constructed from the solution, and a more general solution is determined using transmitted data and received data, that is, the inverse problem is solved.

More specifically, the Green's function necessary for visualization is set first. A function that becomes a solution of this Green's function is then introduced. Next, a partial differential equation in seven-dimensional space (t, $x_1$, $x_2$, $y_1$, $y_2$, $z_1$, $z_2$) the exact solution (the function) of which is the above-mentioned function is constructed. This partial differential equation is then solved using, as a boundary condition, the transmitted data of waves radiated from the transmitting antenna elements arranged on a curved surface and the received data of waves received by the receiving antenna elements arranged on the curved surface, and a visualization function is determined where $t \to 0$, $x_1 \to x_2$ ($=x$), $z_2 \to z_1$ ($=z$), and $y_1 \to y_2$ ($=y$). Thus, the visualization function is determined, allowing information on the interior of an object, such as a flaw inside a tunnel, to be visualized in a versatile manner at high speed.

A specific example is as follows.

1. Inverse Problem of Scattering and the Green's Function

Suppose a situation where waves radiated from $r_1$ are reflected off a point $\xi$ and travel to a point $r_2$ as in FIG. 14. Under the condition that a frequency $\omega$ is constant, the wave transmitting point $r_1$ and the wave receiving point $r_2$ freely move on a curved surface while the wave transmitting point $r_1$ and the wave receiving point $r_2$ satisfy a certain constraint. Data obtained in this case is denoted by $G(r_1, r_2, \omega)$. This function relates to distribution of reflection points within a region. At this time, an angular frequency $\omega=2\pi f$. $G(r_1, r_2, \omega)$ is a sum of reflected signals from all the points $\xi$. Since there are many reflection points within the region, $G(r_1, r_2, \omega)$ can be thought of as in Expression 1 indicated in Embodiment 1.

Note that in this embodiment, the constraint that restricts the wave transmitting point $r_1$ and the wave receiving point $r_2$ is a condition that $r_1$ and $r_2$ move on a curved surface.

A theoretical structure of the inverse problem of scattering is described using this function $G(r_1, r_2, \omega)$.

2. Derivation of Inverse Problem $L(\partial/\partial t, \partial/\partial r_1, \partial/\partial r_2)$ of Scattering in Arbitrary Curved Surface Hereinafter, a method of determining this differential operator is described. In the analysis model according to this embodiment, the transmitting point and the receiving point move on a curved surface unlike in the analysis model according to Embodiment 1. On the curved surface, the x-, y-, and z-coordinates of $r_1$ are not necessarily equal to those of $r_2$. Specifically, $r_1=(x_1, y_1, z_1)$ and $r_2=(x_2, y_2, z_2)$. A function G is defined as in Expression 4 indicated in Embodiment 1, and Expression 37 below is obtained by determining an equation which $G(r_1, r_2, \omega)$ satisfies is determined using $r_1=(x_1, y_1, z_1)$ and $r_2=(x_2, y_2, z_2)$. In Expression 37, $\phi$ corresponds to a function (a solution) for reconstructing an image relating to information on the interior of an object according to the present invention, that is, a function defined in Expression D according to the present invention.

[Math. 39]

$$\phi(x_1, x_2, y_1, y_2, z_1, z_2, \omega) = \quad \text{Expression 37}$$

$$\iint_D \frac{e^{ik\rho_1}}{\rho_1} \frac{e^{ik\rho_2}}{\rho_2} \varepsilon(\xi, \eta, \zeta) d\xi d\eta d\zeta$$

$$\rho_1 = \sqrt{(x_1-\xi)^2 + (y_1-\eta)^2 + (z_1-\zeta)^2}$$

$$\rho_2 = \sqrt{(x_2-\xi)^2 + (y_2-\eta)^2 + (z_2-\zeta)^2}$$

Herein, it is assumed that a time factor is proportional to $\exp(-i\omega t)$, and wave number is denoted by k. Coordinates $x_1$, $x_2$, $y_1$, $y_2$, $z_1$, and $z_2$ are each on an arbitrary curved surface. In this case, the following relationships hold: $\omega=ck$ and $k=2\pi/\lambda$ where c is a speed of propagation and k is wave number. Coordinates $\xi$, $\eta$, and $\zeta$ represent an arbitrary point.

The function in the term to be integrated in the above expression is [Math. 40] in Expression 4 and represented as Expression 6.

$$\varphi \quad \text{[Math. 40]}$$

Here, a partial differential equation the asymptotic solution (the function) of which is Expression 37 is determined. In order for this to be done, high-order terms are ignored in calculation for $1/\rho$ resulting from differentiation. Hereinafter, an abridged notation for differentiation is defined as Expression 38 below.

[Math. 41]

$$\frac{\partial}{\partial t} \to \partial_t, \frac{\partial}{\partial x_1} \to \partial_{x_1}, \frac{\partial}{\partial x_2} \to \partial_{x_2}, \frac{\partial}{\partial y_1} \to \partial_{y_1}, \quad \text{Expression 38}$$

$$\frac{\partial}{\partial y_2} \to \partial_{y_2}, \frac{\partial}{\partial z_1} \to \partial_{z_1}, \frac{\partial}{\partial z_2} \to \partial_{z_2}$$

With this, $\phi$ satisfies the equation represented in Expression 39 below by the same or similar calculation as in Embodiment 1. This Expression 39 corresponds to the scattered field equation according to the present invention. Furthermore, this Expression 39 corresponds to a function defined in Expression E according to the present invention.

[Math. 42]

$$\{\Delta_6 - 2(ik)^2\}\phi = \{(\partial_{x_1}^2 + \partial_{x_2}^2 + \partial_{y_1}^2 + \partial_{y_2}^2 + \partial_{z_1}^2 + \partial_{z_2}^2) - 2(ik)^2\}\phi = 0 \quad \text{Expression 39}$$

Next, a solution of Expression 39 is determined assuming that a time factor of $\phi$ is proportional to $\exp(-i\omega t)$. First, the multi-dimensional Fourier transform of $\phi$ with respect to t, $x_1$, $x_2$, $y_1$, and $y_2$ results in Expression 40 below.

[Math. 43]

$$\tilde{\phi}(k_{x_1}, k_{x_2}, k_{y_1}, k_{y_2}, z_1, z_2, \omega) = \int_{-\infty}^{\infty} e^{i\omega t} dt \int_{-\infty}^{\infty} e^{ik_{y_1} y_1} dy_1 \int_{-\infty}^{\infty} e^{ik_{y_2} y_2} dy_2 \int_{-\infty}^{\infty} e^{ik_{x_1} x_1} dx_1 \int_{-\infty}^{\infty} e^{ik_{x_2} x_2} \phi(x_1, x_2, y_1, y_2, z_1, z_2, t) dx_2$$

Expression 40

Note that the use of a fast Fourier transform makes it possible to obtain analysis data at high speed. Thus, analysis time can be shortened.

Assuming that partial differentials of $z_1$ and $z_2$ are $Dz_1$ and $Dz_2$, respectively, Expression 41 below is obtained.

[Math. 44]

$$\{(D_{z_1}^2 + D_{z_2}^2 - k_{x_1}^2 - k_{x_2}^2 - k_{y_1}^2 - k_{y_2}^2) + 2k^2\}\tilde{\phi} = 0$$

Expression 41

This equation, which is to be solved, has two variables $z_1$ and $z_2$. Therefore, in order to solve Expression 41, a boundary condition for fixed $(x_1, x_2, y_1, y_2)$ or $(k_{x1}, k_{x2}, k_{y1}, k_2)$ is necessary which is given in a one-dimensional region within $(z_1, z_2)$ space.

However, a boundary condition obtained by measurement with the radar is that only given at one point $\{f(x_1, y_1), f(x_2, y_2)\}$ within the $(z_1, z_2)$ space.

Therefore, in order to solve this problem, consistency is required between the present theory and the theory held in the case where $z_1 = z$ and $z_2 = z$. Specifically, the present theory in which and $z_2$ are independent is required to include special solutions $z_1 = z$ and $z_2 = z$.

Assume that a solution of Expression 41 is Expression 42 below.

[Math. 45]

$$E(k_{x_1}, k_{x_2}, k_{y_1}, k_{y_2}, z_1, z_2) = \exp(is_1 z_1)\exp(is_2 z_2)$$

Expression 42

When $z_1 = z$ and $z_2 = z$, Expression 42 becomes Expression 43 below.

[Math. 46]

$$s_1^2 + s_2^2 + k_{x_1}^2 + k_{x_2}^2 + k_{y_1}^2 + k_{y_2}^2 - 2k^2 = 0$$

Expression 43

In the meantime, another equation is necessary as the boundary condition. Here, Expression 44 below is derived from the above-mentioned consistency requirement.

[Math. 47]

$$s_1 + s_2 = \sqrt{k^2 - k_{x_1}^2 - k_{y_1}^2} + \sqrt{k^2 - k_{x_2}^2 - k_{y_2}^2}$$

Expression 44

Using Expression 43 and Expression 44, $s_1$ and $s_2$ are determined to be those represented in Expression 45 below.

[Math. 48]

$$s_1 = \sqrt{k^2 - k_{x_1}^2 - k_{y_1}^2}$$

$$s_2 = \sqrt{k^2 - k_{x_2}^2 - k_{y_2}^2}$$

Expression 45

A solution of the equation can be written as Expression 46 below using these $s_1(k_x, k_{y1}, k_{y2})$ and $s_2(k_x, k_{y1}, k_{y2})$.

[Math. 49]

$$\phi(x_1, x_2, y_1, y_2, z_1, z_2, k) = \frac{1}{(2\pi)^4} \int_{-\infty}^{\infty}\int_{-\infty}^{\infty}\int_{-\infty}^{\infty}\int_{-\infty}^{\infty} e^{-i(k_{x_1} x_1 + k_{x_2} x_2 + k_{y_1} y_1 + k_{y_2} y_2)} a(k_{x_1}, k_{x_2}, k_{y_1}, k_{y_2}) \cdot e^{is_1(k_{x_1}, k_{x_2}, k_{y_1}, k_{y_2})z_2} dk_{x_1} dk_{x_2} dk_{y_1} dk_{y_2}$$

Expression 46

Furthermore, assume that an equation of a curved surface S is, for example, Expression 47 below.

[Math. 50]

$$z = f(x, y)$$

Expression 47

In this case, the boundary condition given on the curved surface S is Expression 48 below.

[Math. 51]

$$\phi(x_1, x_2, y_1, y_2, f(x_1, y_1), f(x_2, y_2), k) = \frac{1}{(2\pi)^4} \int_{-\infty}^{\infty}\int_{-\infty}^{\infty}\int_{-\infty}^{\infty}\int_{-\infty}^{\infty} e^{-i(k_{x_1} x_1 + k_{x_2} x_2 + k_{y_1} y_1 + k_{y_2} y_2)} a(k_{x_1}, k_{x_2}, k_{y_1}, k_{y_2}) \cdot e^{i\{s_1(k_{x_1}, k_{x_2}, k_{y_1}, k_{y_2})f(x_1, y_1) + s_2(k_{x_1}, k_{x_2}, k_{y_1}, k_{y_2})f(x_2, y_2)\}} dk_{x_1} dk_{x_2} dk_{y_1} dk_{y_2}$$

Expression 48

This equation is used to determine $a(k_{x1}, k_{x2}, k_{y1}, k_{y2})$. Here, the abridged notations indicated in Expression 49 below are used.

[Math. 52]

$$a(k) = a(k_{x_1}, k_{x_2}, k_{y_1}, k_{y_2})$$

$$s_1(k) = s_1(k_{x_1}, k_{x_2}, k_{y_1}, k_{y_2})$$

$$s_2(k) = s_2(k_{x_1}, k_{x_2}, k_{y_1}, k_{y_2})$$

Expression 49

Using the abridged notations indicated in Expression 49, Expression 48 becomes an integral equation with respect to $a(k_{x1}, k_{x2}, k_{y1}, k_{y2})$ indicated in Expression 50 below.

[Math. 53]

$$\phi(x_1, x_2, y_1, y_2, f(x_1, y_1), f(x_2, y_2), k) = \frac{1}{(2\pi)^4} \int_{-\infty}^{\infty}\int_{-\infty}^{\infty}\int_{-\infty}^{\infty}\int_{-\infty}^{\infty} e^{-i(k_{x_1} x_1 + k_{x_2} x_2 + k_{y_1} y_1 + k_{y_2} y_2)} a(k) e^{i\{s_1(k)f(x_1, y_1) + s_2(k)f(x_2, y_2)\}} dk$$

Expression 50

If $a(k)$ can be determined from this expression, a solution of the equation of Expression 39 is represented as Expression 51 below based on Expression 46.

[Math. 54]

$$\phi(x_1, x_2, y_1, y_2, z_1, z_2, k) = \frac{1}{(2\pi)^4} \int_{-\infty}^{\infty}\int_{-\infty}^{\infty}\int_{-\infty}^{\infty}\int_{-\infty}^{\infty} e^{-i(k_{x_1} x_1 + k_{x_2} x_2 + k_{y_1} y_1 + k_{y_2} y_2)} a(k) e^{is_1(k)z_1} e^{is_2(k)z_2} dk$$

Expression 51

The Fourier transform of Expression 51 with respect to k where $z_1=z_2=z$ results in a function represented in Expression 52 below.

[Math. 55]

$$\rho(r) = \lim_{t \to 0}\left[\frac{1}{2\pi}\int_{-\infty}^{\infty} \phi(x, x, y, y, z, z, k)e^{-ickt}dk\right] \quad \text{Expression 52}$$

Thus, a final visualization function $\rho(r)$ is obtained.

3. Solution of Integral Equation (Expression 50)

Next, a solution of the above-mentioned Expression 50 is determined. Specifically, approximate data at an arbitrary point in the plane z=0 is determined from data measured at points $P_I$ and $P_J$ on the curved surface S.

For $\phi$ in Expression 50, data $\phi(x_I, x_J, y_I, y_J, z_I, z_J, t)$ measured at the points $P_I$ and $P_J$ on the curved surface S is Fourier transformed, and assume that resultant $\phi_{I,J}(x_I, x_J, y_I, y_J, k)$ is Expression 53 below.

[Math. 56]

$$\Phi_{I,J}(x_I, x_J, y_I, y_J, k) = \int_{-\infty}^{\infty} e^{-ikt}\phi(x_I, x_J, y_I, y_J, z_I, z_J, t)dt \quad \text{Expression 53}$$

Furthermore, Expression 54 below is obtained from Expression 46.

[Math. 57]

$$\Phi(x_I, x_J, y_I, y_J, k) = \frac{1}{(2\pi)^4}\int_{-\infty}^{\infty}\int_{-\infty}^{\infty}\int_{-\infty}^{\infty}\int_{-\infty}^{\infty} e^{-i(k_{x_1}x_I + k_{x_2}x_J + k_{y_1}y_I + k_{y_2}y_J)} a_{I,J}(k_{x_1}, k_{x_2}, k_{y_1}, k_{y_2}, k) \cdot e^{is_1(k, k_{x_1}, k_{x_2}, k_{y_1}, k_{y_2})z_I} e^{is_2(k, k_{x_1}, k_{x_2}, k_{y_1}, k_{y_2})z_J} dk_{x_1} dk_{x_2} dk_{y_1} dk_{y_2} \quad \text{Expression 54}$$

This Expression 54 can be written as Expression 55 below by way of interpretation.

[Math. 58]

$$\Phi(x_I, x_J, y_I, y_J, k)\delta(x_1 - x_I)\delta(x_2 - x_J)\delta(y_1 - y_I)\delta(y_2 - y_J) = \frac{1}{(2\pi)^4}\int_{-\infty}^{\infty}\int_{-\infty}^{\infty} e^{-i(k_{x_1}x_1 + k_{x_2}x_2 + k_{y_1}y_1 + k_{y_2}y_2)} a_{I,J}(k_{x_1}, k_{x_2}, k_{y_1}, k_{y_2}, k) \cdot e^{is_1(k, k_{x_1}, k_{x_2}, k_{y_1}, k_{y_2})z_I} e^{is_2(k, k_{x_1}, k_{x_2}, k_{y_1}, k_{y_2})z_J} dk_{x_1} dk_{x_2} dk_{y_1} dk_{y_2} \quad \text{Expression 55}$$

When both sides of Expression 55 are Fourier transformed and the both sides of resultant Expression 55 are integrated, Expression 56 below is obtained.

[Math. 59]

$$\Phi(x_I, x_J, y_I, y_J, k)e^{i(k_{x_1}x_I + k_{x_2}x_J + k_{y_1}y_I + k_{y_2}y_J)} = a_{I,J}(k_{x_1}, k_{x_2}, k_{y_1}, k_{y_2}, k)e^{is_1(k, k_{x_1}, k_{x_2}, k_{y_1}, k_{y_2})z_I} e^{is_2(k, k_{x_1}, k_{x_2}, k_{y_1}, k_{y_2})z_J} \quad \text{Expression 56}$$

In this way, $a_{I,J}$ is obtained as in Expression 57 below.

[Math. 60]

$$a_{I,J}(k_{x_1}, k_{x_2}, k_{y_1}, k_{y_2}, k) = \Phi(x_I, x_J, y_I, y_J, k) e^{i(k_{x_1}x_I + k_{x_2}x_J + k_{y_1}y_I + k_{y_2}y_J)} e^{-is_1(k, k_{x_1}, k_{x_2}, k_{y_1}, k_{y_2})z_I} e^{-is_2(k, k_{x_1}, k_{x_2}, k_{y_1}, k_{y_2})z_J} \quad \text{Expression 57}$$

When a sum of all values for I and J is obtained, Expression 58 below is obtained.

[Math. 61]

$$a(k_{x_1}, k_{x_2}, k_{y_1}, k_{y_2}, k) = \sum_{I,J} a_{I,J}(k_{x_1}, k_{x_2}, k_{y_1}, k_{y_2}, k) \quad \text{Expression 58}$$

$$= \sum_{I,J} e^{i(k_{x_1}x_I + k_{x_2}x_J + k_{y_1}y_I + k_{y_2}y_J)} e^{-is_1(k, k_{x_1}, k_{x_2}, k_{y_1}, k_{y_2})z_I} e^{-is_2(k, k_{x_1}, k_{x_2}, k_{y_1}, k_{y_2})z_J} \Phi(x_I, x_J, y_I, y_J, k)$$

In this way, conversion into a boundary condition in the plane z=0 can be achieved.

When a solution of the partial differential equation of Expression 39 is obtained using the boundary condition where z=0, Expression 58 is substituted for Expression 46, and Expression 59 below is then obtained. This Expression 59 leads to the above-described Expression 52, which corresponds to a visualization function defined in Expression F according to the present invention.

[Math. 62]

$$\phi(x_1, x_2, y_1, y_2, z_1, z_2, k) = \frac{1}{(2\pi)^4}\int_{-\infty}^{\infty}\int_{-\infty}^{\infty}\int_{-\infty}^{\infty}\int_{-\infty}^{\infty} e^{-i(k_{x_1}x_1 + k_{x_2}x_2 + k_{y_1}y_1 + k_{y_2}y_2)} a(k_{x_1}, k_{x_2}, k_{y_1}, k_{y_2}, k) \cdot e^{is_1(k_{x_1}, k_{x_2}, k_{y_1}, k_{y_2})z_1} e^{is_2(k_{x_1}, k_{x_2}, k_{y_1}, k_{y_2})z_2} dk_{x_1} dk_{x_2} dk_{y_1} dk_{y_2} \quad \text{Expression 59}$$

This visualization function is used to reconstruct an image relating to information on the interior of an object. Thus, it is possible to visualize or image information on the interior of an object, such as a flaw inside the object, in a versatile manner at high speed. Furthermore, since the function $\rho(r)$ is set for three-dimensional space in the reconstructing, information on the interior of an object having a curved surface with high curvature can be more accurately visualized at high speed.

As described above, in the scattering tomography method according to this embodiment, a partial differential equation for the inverse problem is set in an analytical model in which a sensor is arranged on an arbitrary curved surface, and solving this equation leads to a visualization function. With this, in a scattering tomography method for analyzing scattered waves of waves radiated to an object, information on the interior of an object having a curved surface with high curvature can be visualized in a versatile manner at high speed.

Particularly, in this embodiment, a visualization function is derived in the scattering tomography method that is applied in the case where the sensor of the multi-path array radar is a two-dimensional sensor array. Therefore, it is possible to obtain a reconstructed image at high speed because, according to this visualization function, the number of mechanical scanning processes is less than in the case described in Embodiment 1 where the sensor of the multi-path array radar is a one-dimensional sensor array.

Note that the above arithmetic expressions and process flow of deriving the arithmetic expressions are one example; other arithmetic expressions and other deriving process flow may be used.

Although the electromagnetic waves are used as the waves in this embodiment, the electromagnetic waves may be rearranged by ultrasonic waves or the like. Furthermore, although periodic waves having a predetermined frequency are used in this embodiment because the electromagnetic waves are used, the waves may be pulsed waves or the like instead of the periodic waves.

Furthermore, although the tunnel lining concrete is cited as an example of an object in this embodiment, the object is not limited to the tunnel lining concrete and may be other object.

Hereinbefore the scattering tomography method and the scattering tomography device according to the present invention have been described based on the embodiments, but the present invention is not limited to these embodiments. The scope of the present invention may also include embodiments as a result of adding various modifications to the embodiments that may be conceived by those skilled in the art, and other embodiments obtained by combining structural elements in the embodiments in any manner.

For example, in the scattering tomography device, a process which a specific processing unit performs may be performed by another processing unit. Furthermore, in the scattering tomography method, the process sequence may be changed, and a plurality of processes may be performed in parallel.

A step in the scattering tomography method according to the present invention may be performed by a computer. Furthermore, the present invention may be provided as a program for causing a computer to perform a step included in the scattering tomography method. Moreover, the present invention may be provided as a non-transitory, computer-readable recording medium such as a compact disc read-only memory (CD-ROM) on which the program has been recorded.

A plurality of structural elements included in the scattering tomography device may be provided as large scale integration (LSI), which is an integrated circuit. These structural elements may be individually configured as single chips or may be configured so that a part or all of the structural elements are included in a single chip. The name used here is LSI, but it may also be called an integrated circuit (IC), system LSI, super LSI, or ultra LSI depending on the degree of integration.

Moreover, ways to achieve integration are not limited to the LSI, and a dedicated circuit or a general-purpose processor can also achieve the integration. A field programmable gate array (FPGA) which allows programming or a reconfigurable processor which allows reconfiguration of the connections and settings of the circuit cells inside the LSI may also be used.

Furthermore, when advancement in semiconductor technology or derivatives of other technologies brings forth a circuit integration technology which replaces LSI, it will be appreciated that such a circuit integration technology may be used to integrate the structural elements included in the scattering tomography device.

INDUSTRIAL APPLICABILITY

A scattering tomography method and a scattering tomography device according to the present invention are useful for inspection of an object with high curvature and are applicable to, for example, inspection of a flaw inside a railway tunnel for Zairaisen local trains, radar inspection of concrete lining on roads, inspection of reinforcing steel inside concrete for corrosion, inspection of reinforcing steel structures for seismic resistance in a disaster area, and medical diagnosis.

REFERENCE SIGNS LIST

10 Antenna element
20 Multi-path array radar (Scattering tomography device)
30 Sensor
31 Transmitter
32 Receiver
36 Transmitting antenna element
37 Receiving antenna element
40 Image reconstructor
50 Monitor

The invention claimed is:

1. A scattering tomography method performed by a scattering tomography device of analyzing scattered waves of waves radiated to an object, the scattering tomography method comprising:

radiating electromagnetic waves to the object from a plurality of transmitting antenna elements arranged in a line on a curved surface;

receiving scattered waves by a plurality of receiving antenna elements arranged in a line proximate to the line of the plurality of transmitting antenna elements on the curved surface;

reconstructing a three-dimensional image relating to information on an interior of the object using, as a boundary condition, scattered wave data representing the scattered waves received by the receiving antenna elements; and displaying a reconstructed three-dimensional image that is reconstructed in the reconstructing on a display, wherein in the radiating and receiving, the line of the plurality of transmitting antenna elements is along with the line of the plurality of receiving antenna elements, and the line of the plurality of transmitting antenna elements and the line of the plurality of receiving antenna elements move in an x axis direction and rotate around the object so that the object is scanned, wherein in the reconstructing:

a function $\phi$, set for three-dimensional space, for reconstructing the three-dimensional image relating to the information on the interior of the object is set in advance, the function $\phi$ being defined in Expression A;

an equation which the function $\phi$ satisfies in $(x, y_1, y_2, z_1, z_2)$ space is constructed, the equation being defined in Expression B;

a visualization function $\rho$ that is obtained by solving the equation is derived from the scattered wave data, the visualization function $\rho$ being defined in Expression C, the scattered wave data being obtained by measurement; and the three-dimensional image relating to the information on the interior of the object is reconstructed using the visualization function $\rho$,

[Math. 63]

$$\phi(x, y_1, y_2, z_1, z_2, \omega) = \int\int\int_D \frac{e^{ik\rho_1}}{\rho_1} \frac{e^{ik\rho_2}}{\rho_2} \varepsilon(\xi, \eta, \zeta) d\xi d\eta d\zeta \quad \text{Expression A}$$

$$\rho_1 = \sqrt{(x-\xi)^2 + (y_1-\eta)^2 + (z_1-\zeta)^2}$$

$$\rho_2 = \sqrt{(x-\xi)^2 + (y_2-\eta)^2 + (z_2-\zeta)^2}$$

[Math. 64]

$$\left[\frac{1}{4}\Delta_5^2 - \frac{1}{c^2}\partial_t^2 \partial_x^2 - (\partial_{y_1}^2 + \partial_{z_1}^2)(\partial_{y_2}^2 + \partial_{z_2}^2)\right]\phi = 0 \quad \text{Expression B}$$

[Math. 65]

$$\rho(r) = \lim_{t\to 0}\left[\frac{1}{2\pi}\int_{-\infty}^{\infty} \phi(x, y, z, z, k)e^{-ickt} dk\right] \quad \text{Expression C}$$

where in Expression A to Expression C: x, $y_1$, $y_2$, $z_1$, and $z_2$ are each a coordinate on an arbitrary curve; $\xi$, $\eta$, and $\zeta$ are an x-coordinate, a y-coordinate, and a z-coordinate, respectively, of an arbitrary scattering point within a region; c is a speed of propagation; k is wave number; and $\omega=ck$, $\varepsilon(\xi,\eta,\zeta)$ is a function of a dielectric constant, and wherein the plurality of transmitting antenna elements and the plurality of receiving antenna elements are part of a multi-path curvilinear array radar, wherein Expression B depends on time, wherein in the reconstructing:

a coordinate of a transmitting point of the radiated wave is represented as $p_1(x,y_1,z_1)$, a coordinate of a receiving point of the scattered wave is represented as $p_2(x,y_2,z_2)$, and the scattered wave data is written as Expression A;

the scattered wave data is analyzed on the assumption that x coordinate of the transmission point and x coordinate of the receiving point are the same as each other;

$a(k_x,k_{y1},k_{y2},k)$ is derived in the $(x,y_1,y_2,z_1,z_2)$ space by using the scattered wave data measured on the curved surface of the object on the basis of Expression G and Expression H;

a solution of Expression B which is represented as Expression I is derived by using $a(k_x,k_{y1},k_{y2},k)$;

a formula is derived by the taking the limit $y_1 \to y$ of the solution on the basis of Expression J; and the visualization function $\rho$ is derived by integrating the formula with respect to k in all range on the basis of Expression K, $$a(k_x, k_{y_1}, k_{y_2}, k) = \sum_{I,J} a_{I,J}(k_x, k_{y_1}, k_{y_2}, k) \quad \text{Expression G}$$

$$= \sum_{I,J} e^{i(k_{y_1} y_I + k_{y_2} y_J)} e^{-is_1(k,k_x,k_{y_1},k_{y_2})z_I}$$

$$e^{-is_2(k,k_x,k_{y_1},k_{y_2})z_J} \Phi(k_x, y_I, y_J, k)$$

$$s_1(k_x, k_{y_1}, k_{y_2}) = \frac{\sqrt{k^2-k_{y_1}^2}\sqrt{\left(\sqrt{k^2-k_{y_1}^2}+\sqrt{k^2-k_{y_2}^2}\right)^2-k_x^2}}{\sqrt{k^2-k_{y_1}^2}+\sqrt{k^2-k_{y_2}^2}} \quad \text{Expression H}$$

$$s_2(k_x, k_{y_1}, k_{y_2}) = \frac{\sqrt{k^2-k_{y_2}^2}\sqrt{\left(\sqrt{k^2-k_{y_1}^2}+\sqrt{k^2-k_{y_2}^2}\right)^2-k_x^2}}{\sqrt{k^2-k_{y_1}^2}+\sqrt{k^2-k_{y_2}^2}}$$

$$\frac{1}{(2\pi)^3}\int_{-\infty}^{\infty}\int_{-\infty}^{\infty}\int_{-\infty}^{\infty} e^{-i(k_x x + k_{y_1} y_1 + k_y y)} \quad \text{Expression I}$$

$$a(k_x, k_{y_1}, k_y, k)e^{j\left\{\sqrt{\left(\sqrt{k^2-k_{y_1}^2}+\sqrt{k^2-k_y^2}\right)^2-k_x^2}\right\}z} dk_x dk_{y_1} dk_y$$

$$\phi(x, y, y, z, k) = \lim_{y_1 \to y}\left[\frac{1}{(2\pi)^3}\right. \quad \text{Expression J}$$

$$\int_{-\infty}^{\infty}\int_{-\infty}^{\infty}\int_{-\infty}^{\infty} e^{-i(k_x x + k_{y_1} y_1 + k_y y)} a(k_x, k_{y_1}, k_y, k)$$

$$\left. e^{j\left\{\sqrt{\left(\sqrt{k^2-k_{y_1}^2}+\sqrt{k^2-k_y^2}\right)^2-k_x^2}\right\}z} dk_x dk_{y_1} dk_y \right]$$

$$\rho(x, y, z) = \int_{-\infty}^{\infty} \phi(x, y, y, z, k) dk \quad \text{Expression K}$$

wherein $\Phi(k_x, y_I, y_J, k)$ is the scattered wave data, $k_{y1}$ is wave number of $y_1$, $k_{y2}$ is wave number of $y_2$ and $k_x$ is wave number of x, and wherein the scattered waves are measured on the curved surface of the object, and the curved surface is a boundary surface between in and out of the object.

2. The scattering tomography method according to claim 1, wherein the visualization function is derived using a fast Fourier transform.

3. A scattering tomography method performed by a scattering tomography device of analyzing scattered waves of waves radiated to an object, the scattering tomography method comprising:

radiating electromagnetic waves to the object from a plurality of transmitting antenna elements arranged on a curved surface;

receiving scattered waves by a plurality of receiving antenna elements arranged proximate to the plurality of transmitting antenna elements on the curved surface;

reconstructing a three-dimensional image relating to information on an interior of the object from scattered wave data representing the scattered waves received by the receiving antenna elements; and displaying a reconstructed three-dimensional image that is reconstructed in the reconstructing on a display, wherein in the reconstructing:

a function $\phi$, set for three-dimensional space, for reconstructing the three-dimensional image relating to the information on the interior of the object is set in advance, the function $\phi$ being defined in Expression D;

an equation which the function $\phi$ satisfies in $(x_1,x_2,y_1,y_2,z_1,z_2)$ space is constructed, the equation being defined in Expression E;

a visualization function ρ that is obtained by solving the equation is derived from the scattered wave data, the visualization function ρ being defined in Expression F, the scattered wave data being obtained by measurement; and the three-dimensional image relating to the information on the interior of the object is reconstructed using the visualization function ρ,

[Math. 66]

$$\phi(x_1, x_2, y_1, y_2, z_1, z_2, \omega) = \quad \text{Expression D}$$

$$\int\int\int_D \frac{e^{ik\rho_1}}{\rho_1} \frac{e^{ik\rho_2}}{\rho_2} \varepsilon(\xi, \eta, \zeta) d\xi d\eta d\zeta$$

$$\rho_1 = \sqrt{(x_1-\xi)^2 + (y_1-\eta)^2 + (z_1-\zeta)^2}$$

$$\rho_2 = \sqrt{(x_2-\xi)^2 + (y_2-\eta)^2 + (z_2-\zeta)^2}$$

[Math. 67]

$$\{\Delta_6 - 2(ik)^2\}\phi = \quad \text{Expression E}$$

$$\{(\partial_{x_1}^2 + \partial_{x_2}^2 + \partial_{y_1}^2 + \partial_{y_2}^2 + \partial_{z_1}^2 + \partial_{z_2}^2) - 2(ik)^2\}\phi = 0$$

[Math. 68]

$$\rho(r) = \lim_{t\to 0}\left[\frac{1}{2\pi}\int_{-\infty}^{\infty} \phi(x, x, y, y, z, z, k)e^{-ickt}dk\right] \quad \text{Expression F}$$

where in Expression D to Expression F: $x_1$, $x_2$, $y_1$, $y_2$, $z_1$, and $z_2$ are each a coordinate on an arbitrary curved surface; and are an x-coordinate, a y-coordinate, and a z-coordinate, respectively, of an arbitrary scattering point within a region; c is a speed of propagation; k is wave number; and ω=ck, ε(ξ,η,ζ) is a function of a dielectric constant, and wherein the plurality of transmitting antenna elements and the plurality of receiving antenna elements are part of a multi-path curvilinear array radar and are arranged to configure a two-dimensional sensor array, wherein Expression E depends on k, wherein each of the plurality of transmitting antenna elements and the plurality of receiving antenna elements has a finite size, wherein in the reconstructing:

a coordinate of a transmitting point of the radiated wave is represented as $p_1(x_1,y_1,z_1)$, a coordinate of a receiving point of the scattered wave is represented as $p_2(x_2,y_2,z_2)$, $x_1$ and $x_2$ are different from each other, and the scattered wave data is written as Expression D;

$a(k_{x1},k_{x2},k_{y1},k_{y2},k)$ is derived in the $(x_1,x_2,y_1,y_2,z_1,z_2)$ space by using the scattered wave data measured on the curved surface of the object on the basis of Expression L and Expression M;

a solution of Expression E is derived by using $a(k_{x1},k_{x2},k_{y1},k_{y2},k)$ on the basis of Expression N;

a formula is derived by the taking the limit $x_2 \to x_1 = x$, $y_2 \to y_1 = y$ of the solution; and the visualization function ρ is derived by integrating the formula with respect to k in all range on the basis of Expression F, $$a(k_{x_1}, k_{x_2}, k_{y_1}, k_{y_2}, k) = \sum_{I,J} a_{I,J}(k_{x_1}, k_{x_2}, k_{y_1}, k_{y_2}, k) = \quad \text{Expression L}$$

$$\sum_{I,J} e^{i(k_{y_1} x_I + k_{x_2} x_J + k_{y_1} y_I + k_{y_2} y_J)} e^{-is_1(k_{x_1},k_{x_2},k_{y_1},k_{y_2})z_I}$$

$$e^{-is_2(k,k_{x_1},k_{x_2},k_{y_1},k_{y_2})z_J} \Phi(x_I, x_J, y_I, y_J, k)$$

$$s_1 = \sqrt{k^2 - k_{x_1}^2 - k_{y_1}^2} \quad \text{Expression M}$$

$$s_2 = \sqrt{k^2 - k_{x_1}^2 - k_{y_2}^2}$$

$$\phi(x_1, x_2, y_1, y_2, z_1, z_2, k) = \quad \text{Expression N}$$

$$\frac{1}{(2\pi)^4} \int_{-\infty}^{\infty}\int_{-\infty}^{\infty}\int_{-\infty}^{\infty} e^{-i(k_{x_1}x_1 + k_{x_2}x_2 + k_{y_1}y_1 + k_{y_2}y_2)}$$

$$a(k_{x_1}, k_{x_2}, k_{y_1}, k_{y_2}, k) \cdot e^{is_1(k_{x_1},k_{x_2},k_{y_1},k_{y_2})z_1}$$

$$e^{is_2(k_{x_1},k_{x_2},k_{y_1},k_{y_2})z_2} dk_{x_1} dk_{x_2} dk_{y_1} dk_{y_2}$$

wherein $\Phi(x_I,x_J,y_I,y_J,k)$ is the scattered wave data, $k_{y1}$ is wave number of $y_1$, $k_{y2}$ is wave number of $y_2$, $k_{x1}$ is wave number of $x_1$, and $k_{x2}$ is wave number of $x_2$, and wherein the scattered waves are measured on the curved surface of the object, and the curved surface is a boundary surface between in and out of the object.

4. A scattering tomography device for analyzing scattered waves of waves radiated to an object, the scattering tomography device comprising:

a plurality of transmitting antenna elements that are arranged in a line on a curved surface and radiate electromagnetic waves to the object;

a plurality of receiving antenna elements that are arranged in a line proximate to the line of the plurality of transmitting antenna elements on the curved surface and receive scattered waves which are the radiated waves after having been scattered in the object;

an image reconstructor that reconstructs a three-dimensional image relating to information on an interior of the object from scattered wave data representing the received scattered wave; and a display that displays a reconstructed three-dimensional image that is reconstructed by the image reconstructor, wherein the line of the plurality of transmitting antenna elements is along with the line of the plurality of receiving antenna elements, and the line of the plurality of transmitting antenna elements and the line of the plurality of receiving antenna elements move in an x axis direction and rotate around the object so that the object is scanned, wherein the image reconstructor:

sets in advance a function φ, set in three-dimensional space, for reconstructing the three-dimensional image relating to the information on the interior of the object, the function φ being defined in Expression A;

constructs an equation which the function φ satisfies in $(x,y_1,y_2,z_1,z_2)$ space, the equation being defined in Expression B;

derives, from the scattered wave data, a visualization function ρ that is obtained by solving the equation, the scattered wave data being obtained by measurement, the visualization function ρ being defined in Expression C; and reconstructs, using the visualization function ρ, the three-dimensional image relating to the information on the interior of the object,

[Math. 69]

$$\phi(x, y_1, y_2, z_1, z_2, \omega) = \iint_D \frac{e^{ik\rho_1}}{\rho_1} \frac{e^{ik\rho_2}}{\rho_2} \varepsilon(\xi, \eta, \zeta) d\xi d\eta d\zeta \qquad \text{Expression A}$$

$$\rho_1 = \sqrt{(x-\xi)^2 + (y_1-\eta)^2 + (z_1-\zeta)^2}$$

$$\rho_2 = \sqrt{(x-\xi)^2 + (y_2-\eta)^2 + (z_2-\zeta)^2}$$

[Math. 70]

$$\left[\frac{1}{4}\Delta_5^2 - \frac{1}{c^2}\partial_t^2 \partial_x^2 - (\partial_{y_1}^2 + \partial_{z_1}^2)(\partial_{y_2}^2 + \partial_{z_2}^2)\right]\phi = 0 \qquad \text{Expression B}$$

[Math. 71]

$$\rho(r) = \lim_{t \to 0}\left[\frac{1}{2\pi}\int_{-\infty}^{\infty} \phi(x, y, y, z, k) e^{-ickt} dk\right] \qquad \text{Expression C}$$

where in Expression A to Expression C: x, $y_1$, $y_2$, $z_1$, and $z_2$ are each a coordinate on an arbitrary curve; $\xi$, $\eta$, and $\zeta$ are an x-coordinate, a y-coordinate, and a z-coordinate, respectively, of an arbitrary scattering point within a region; c is a speed of propagation; k is wave number; and $\omega = ck$, $\varepsilon(\xi, \eta, \zeta)$ is a function of a dielectric constant, and wherein the plurality of transmitting antenna elements and the plurality of receiving antenna elements are part of a multi-path curvilinear array radar, wherein Expression B depends on time, wherein a coordinate of a transmitting point of the radiated wave is represented as $p_1(x, y_1, z_1)$, a coordinate of a receiving point of the scattered wave is represented as $p_2(x, y_2, z_2)$, and the scattered wave data is written as Expression A, wherein in the image reconstructor:

analyzes the scattered wave data on the assumption that x coordinates of a transmission point of and that of the receiving point are the same as each other;

derives $a(k_x, k_{y_1}, k_{y_2}, k)$ in the $(x, y_1, y_2, z_1, z_2)$ space by using the scattered wave data measured on the curved surface of the object on the basis of Expression G and Expression H;

derives a solution of Expression B which is represented as Expression I by using $a(k_x, k_{y_1}, k_{y_2}, k)$;

derives a formula by the taking the limit $y_1 \to y$ of the solution on the basis of Expression J; and derives the visualization function $\rho$ by integrating the formula with respect to k in all range on the basis of Expression K, $$a(k_x, k_{y_1}, k_{y_2}, k) = \sum_{I,J} a_{I,J}(k_x, k_{y_1}, k_{y_2}, k) \qquad \text{Expression G}$$

$$= \sum_{I,J} e^{i(k_{y_1} y_I + k_{y_2} y_J)} e^{-is_1(k, k_x, k_{y_1}, k_{y_2})z_I}$$

$$\cdot e^{-is_2(k, k_x, k_{y_1}, k_{y_2})z_J} \Phi(k_x, y_I, y_J, k)$$

$$s_1(k_x, k_{y_1}, k_{y_2}) = \frac{\sqrt{k^2 - k_{y_1}^2} \sqrt{\left(\sqrt{k^2 - k_{y_1}^2} + \sqrt{k^2 - k_{y_2}^2}\right)^2 - k_x^2}}{\sqrt{k^2 - k_{y_1}^2} + \sqrt{k^2 - k_{y_2}^2}} \qquad \text{Expression H}$$

$$s_2(k_x, k_{y_1}, k_{y_2}) = \frac{\sqrt{k^2 - k_{y_2}^2} \sqrt{\left(\sqrt{k^2 - k_{y_1}^2} + \sqrt{k^2 - k_{y_2}^2}\right)^2 - k_x^2}}{\sqrt{k^2 - k_{y_1}^2} + \sqrt{k^2 - k_{y_2}^2}}$$

-continued $$\frac{1}{(2\pi)^3}\int_{-\infty}^{\infty}\int_{-\infty}^{\infty}\int_{-\infty}^{\infty} e^{-i(k_x x + k_{y_1} y_1 + k_y y)} \qquad \text{Expression I}$$

$$a(k_x, k_{y_1}, k_y, k) e^{j\left\{\sqrt{\left(\sqrt{k^2-k_{y_1}^2}+\sqrt{k^2-k_y^2}\right)^2 - k_x^2}\right\}z} dk_x dk_{y_1} dk_y$$

$$\phi(x, y, y, z, k) = \lim_{y_1 \to y}\left[\frac{1}{(2\pi)^3}\right. \qquad \text{Expression J}$$

$$\int_{-\infty}^{\infty}\int_{-\infty}^{\infty}\int_{-\infty}^{\infty} e^{-i(k_x x + k_{y_1} y_1 + k_y y)} a(k_x, k_{y_1}, k_y, k)$$

$$\left. e^{j\left\{\sqrt{\left(\sqrt{k^2-k_{y_1}^2}+\sqrt{k^2-k_y^2}\right)^2 - k_x^2}\right\}z} dk_x dk_{y_1} dk_y\right]$$

$$\rho(x, y, z) = \int_{-\infty}^{\infty} \phi(x, y, y, z, k) dk \qquad \text{Expression K}$$

wherein $\Phi(k_x, y_I, y_J, k)$ is the scattered wave data, $k_{y_1}$ is wave number of $y_1$, $k_{y_2}$ is wave number of $y_2$, and $k_x$ is wave number of x, and wherein the scattered waves are measured on the curved surface of the object, and the curved surface is a boundary surface between in and out of the object.

5. The scattering tomography device according to claim 4, wherein the image reconstructor derives the visualization function using a fast Fourier transform.

6. A scattering tomography device for analyzing scattered waves of waves radiated to an object, the scattering tomography device comprising:

a plurality of transmitting antenna elements that are arranged on a curved surface and radiate electromagnetic waves to the object;

a plurality of receiving antenna elements that are arranged proximate to the plurality of transmitting antenna elements on the curved surface and receive scattered waves which are the radiated waves after having been scattered in the object; and an image reconstructor that reconstructs a three-dimensional image relating to information on an interior of the object from scattered wave data representing the received scattered wave; and a display that displays a reconstructed three-dimensional image that is reconstructed by the image reconstructor, wherein the image reconstructor:

sets in advance a function $\phi$, set for three-dimensional space, for reconstructing the three-dimensional image relating to the information on the interior of the object, the function $\phi$ being defined in Expression D;

constructs an equation which the function $\phi$ satisfies in $(x_1, x_2, y_1, y_2, z_1, z_2)$ space, the equation being defined in Expression E;

derives, from the scattered wave data, a visualization function $\rho$ that is obtained by solving the equation, the scattered wave data being obtained by measurement, the visualization function $\rho$ being defined in Expression F; and reconstructs, using the visualization function $\rho$, the three-dimensional image relating to the information on the interior of the object,

[Math. 72]

$$\phi(x_1, x_2, y_1, y_2, z_1, z_2, \omega) = \quad \text{Expression D}$$
$$\int\int_D \frac{e^{ik\rho_1}}{\rho_1}\frac{e^{ik\rho_2}}{\rho_2}\varepsilon(\xi,\eta,\zeta)d\xi d\eta d\zeta$$
$$\rho_1 = \sqrt{(x-\xi)^2 + (y_1-\eta)^2 + (z_1-\zeta)^2}$$
$$\rho_2 = \sqrt{(x-\xi)^2 + (y_2-\eta)^2 + (z_2-\zeta)^2}$$

[Math. 73]

$$\{\Delta_6 - 2(ik)^2\}\phi = \quad \text{Expression E}$$
$$\{(\partial_{x_1}^2 + \partial_{x_2}^2 + \partial_{y_1}^2 + \partial_{y_2}^2 + \partial_{z_1}^2 + \partial_{z_2}^2) - 2(ik)^2\}\phi = 0$$

[Math. 74]

$$\rho(r) = \lim_{t\to 0}\left[\frac{1}{2\pi}\int_{-\infty}^{\infty}\phi(x,x,y,y,z,z,k)e^{-ickt}dk\right] \quad \text{Expression F}$$

where in Expression D to Expression F: $x_1$, $x_2$, $y_1$, $y_2$, $z_1$, and $z_2$ are each a coordinate on an arbitrary curved surface; and are an x-coordinate, a y-coordinate, and a z-coordinate, respectively, of an arbitrary scattering point within a region; c is a speed of propagation; k is wave number; and $\omega=ck$, $\varepsilon(\xi,\eta,\zeta)$ is a function of a dielectric constant, and wherein the plurality of transmitting antenna elements and the plurality of receiving antenna elements are part of a multi-path curvilinear array radar and are arranged to configure a two-dimensional sensor array, wherein Expression E depends on k, wherein each of the plurality of transmitting antenna elements and the plurality of receiving antenna elements has a finite size, wherein a coordinate of a transmitting point of the radiated wave is represented as $p_1(x_1,y_1,z_1)$, a coordinate of a receiving point of the scattered wave is represented as $p_2(x_2,y_2,z_2)$, $x_1$ and $x_2$ are different from each other, and the scattered wave data is written as Expression D, wherein the image reconstructor:

derives $a(k_{x1},k_{x2},k_{y1},k_{y2},k)$ in the $(x_1,x_2,y_1,y_2,z_1,z_2)$ space by using the scattered wave data measured on the curved surface of the object on the basis of Expression L and Expression M;

derives a solution of Expression E by using $a(k_{x1},k_{x2},k_{y1},k_{y2},k)$ on the basis of Expression N;

derives a formula by the taking the limit $x_2 \to x_1 = x$, $y_2 \to y_1 = y$ of the solution; and derives the visualization function ρ by integrating the formula with respect to k in all range on the basis of Expression F, $$a(k_{x_1},k_{x_2},k_{y_1},k_{y_2},k) = \sum_{I,J} a_{I,J}(k_{x_1},k_{x_2},k_{y_1},k_{y_2},k) = \quad \text{Expression L}$$
$$\sum_{I,J} e^{i(k_{y_1}x_I + k_{x_2}x_J + k_{y_1}y_I + k_{y_2}y_J)} e^{-is_1(k_{x_1},k_{x_2},k_{y_1},k_{y_2})z_I}$$
$$e^{-is_2(k_{x_1},k_{x_2},k_{y_1},k_{y_2})z_J}\Phi(x_I,x_J,y_I,y_J,k)$$

$$s_1 = \sqrt{k^2 - k_{x_1}^2 - k_{y_1}^2} \quad \text{Expression M}$$
$$s_2 = \sqrt{k^2 - k_{x_1}^2 - k_{y_2}^2}$$

$$\phi(x_1,x_2,y_1,y_2,z_1,z_2,k) = \quad \text{Expression N}$$
$$\frac{1}{(2\pi)^4}\int_{-\infty}^{\infty}\int_{-\infty}^{\infty}\int_{-\infty}^{\infty} e^{-i(k_{x_1}x_1 + k_{x_2}x_2 + k_{y_1}y_1 + k_{y_2}y_2)}$$
$$a(k_{x_1},k_{x_2},k_{y_1},k_{y_2},k)\cdot e^{is_1(k_{x_1},k_{x_2},k_{y_1},k_{y_2})z_1}$$
$$e^{is_2(k_{x_1},k_{x_2},k_{y_1},k_{y_2})z_2} dk_{x_1} dk_{x_2} dk_{y_1} dk_{y_2}$$

wherein $\Phi(x_I,x_J,y_I,y_J,k)$ is the scattered wave data with respect to t, $k_{y1}$ is wave number of $y_1$, $k_{y2}$ is wave number of $y_2$, $k_{x1}$ is wave number of $x_1$, and $k_{x2}$ is wave number of $x_2$, and wherein the scattered waves are measured on the curved surface of the object, and the curved surface is a boundary surface between in and out of the object.

* * * * *

UNITED STATES PATENT AND TRADEMARK OFFICE
CERTIFICATE OF CORRECTION

PATENT NO. : 10,578,552 B2
APPLICATION NO. : 14/767094
DATED : March 3, 2020
INVENTOR(S) : Kenjiro Kimura et al.

It is certified that error appears in the above-identified patent and that said Letters Patent is hereby corrected as shown below:

In the Specification

Column 10, Lines 19-20, reads "Since there are many reflection points within the region, G($r_1$, $r_2$, w) can be written as in Expression 1." should read --Since there are many reflection points within the region, G($r_1$, $r_2$, $\omega$) can be written as in Expression 1.--

Column 10, Line 27, reads "the waves radiated from the point $r_1$, reflected off the point" should read --the waves radiated from the point $r_1$, reflected off the point $\xi$,--

Column 10, Line 34, reads "x-coordinate of and the x-coordinate of $r_2$ are always equal." should read --x-coordinate of $r_1$ and the x-coordinate of $r_2$ are always equal.--

Column 10, Line 39, reads "case, the function G($r_1$, $r_2$,w) is a solution of a differential" should read --case, the function G($r_1$, $r_2$, $\omega$) is a solution of a differential--

Column 11, Line 18, please replace equation "$r_1$ = (x, $y_1$, $z_1$) and $r_2$ =$y_2$, $z_2$)" with --$r_1$ = (x, $y_1$, $z_1$) and $r_2$ = (x, $y_2$, $z_2$)--

Column 11, Line 24, replace the [Math 5] equation with the following equation:

[Math. 5]

$$G(\mathbf{r}_1, \mathbf{r}_2, \omega) = \iiint_D \varphi(\mathbf{r}_1 \to \xi \to \mathbf{r}_2, \omega) d\xi$$

Expression 4

Column 13, Lines 30-33, replace the [Math 17] equation with the following equation:

Signed and Sealed this
Twenty-third Day of June, 2020

Andrei Iancu
*Director of the United States Patent and Trademark Office*

[Math. 17]

$$(s_1^2+s_2^2+k_x^2+k_{y_1}^2+k_{y_2}^2)^2-4k^2k_x^2-4(s_1^2+k_{y_1}^2)(s_2^2+k_{y_2}^2)=0$$

Expression 15

Column 15, Line 17, "$z_U$" should read --$z_I$--

Column 20, Line 60, "Embodiment" should read --Embodiment 1.--

Column 22, Lines 60-63, replace [Math 42] equation with the following equation:
[Math. 42]

$$\{\Delta_6-2(ik)^2\}\phi=\{(\partial_{x_1}^2+\partial_{x_2}^2+\partial_{y_1}^2+\partial_{y_2}^2+\partial_{z_1}^2+\partial_{z_2}^2)-2(ik)^2\}\phi=0$$

Expression 39

Column 23, Lines 1-9, replace [Math 43] equation with the following equation:
[Math. 43]

$$\tilde{\phi}(k_{x_1},k_{x_2},k_{y_1},k_{y_2},z_1,z_2,\omega)$$
$$=\int_{-\infty}^{\infty}e^{i\omega t}dt\int_{-\infty}^{\infty}e^{ik_{y_1}y_1}dy_1\int_{-\infty}^{\infty}e^{ik_{y_2}y_2}dy_2\int_{-\infty}^{\infty}e^{ik_{x_1}x_1}dx_1\int_{-\infty}^{\infty}e^{ik_{x_2}x_2}\phi(x_1,x_2,y_1,y_2,z_1,z_2,t)dx_2$$

Expression 40

Column 23, Line 24, "k$_2$)" should read --k$_{y2}$)--

Column 23, Line 32, "which and z$_2$" should read --which z$_1$ and z$_2$--

Column 24, Lines 1-9, replace [Math 49] equation with the following equation:

[Math. 49]

$$\phi(x_1,x_2,y_1,y_2,z_1,z_2,k)$$
$$=\frac{1}{(2\pi)^4}\int_{-\infty}^{\infty}\int_{-\infty}^{\infty}\int_{-\infty}^{\infty}\int_{-\infty}^{\infty} e^{-i(k_{x_1}x_1+k_{x_2}x_2+k_{y_1}y_1+k_{y_2}y_2)} a(k_{x_1},k_{x_2},k_{y_1},k_{y_2})$$
$$\cdot e^{is_1(k_{x_1},k_{x_2},k_{y_1},k_{y_2})z_1} e^{is_2(k_{x_1},k_{x_2},k_{y_1},k_{y_2})z_2} dk_{x_1} dk_{x_2} dk_{y_1} dk_{y_2}$$

Expression 46

In the Claims

In Claim 1, Column 29, Lines 15-20, replace [Math 65] equation with the following equation:
[Math. 65]

$$\rho(\mathbf{r}) = \underset{t\to 0}{Lim}\left[\frac{1}{2\pi}\int_{-\infty}^{\infty}\phi(x,y,y,z,z,k)e^{-ickt}dk\right]$$

Expression C

In Claim 1, Column 30, Lines 12-20, replace Expression I equation with the following equation:

$$\frac{1}{(2\pi)^3}\int_{-\infty}^{\infty}\int_{-\infty}^{\infty}\int_{-\infty}^{\infty} e^{-i(k_x x+k_{y_1}y_1+k_y y)} a(k_x,k_{y_1},k_y,k) e^{i(\sqrt{\sqrt{k^2-k_{y_1}^2}+\sqrt{k^2-k_y^2}})^2-k_x^2)z} dk_x dk_{y_1} dk_y$$

Expression I

In Claim 1, Column 30, Lines 19-30, replace Expression J equation with the following equation:

$$\phi(x,y,y,z,k) = \underset{x_1\to y}{Lim}[\frac{1}{(2\pi)^3}\int_{-\infty}^{\infty}\int_{-\infty}^{\infty}\int_{-\infty}^{\infty} e^{-i(k_x x+k_{y_1}y_1+k_y y)} a(k_x,k_{y_1},k_y,k) e^{i(\sqrt{\sqrt{k^2-k_{y_1}^2}+\sqrt{k^2-k_y^2}})^2-k_x^2)z} dk_x dk_{y_1} dk_y]$$

Expression J

In Claim 1, Column 30, Line 35, "ky$_2$" should read --$k_{y2}$--

In Claim 3, Column 31, Line 34, "surface; and are" should read --surface; ξ, η, and ζ are--

In Claim 3, Column 32, Lines 7-11, replace Expression M equation with the following equation:

$$s_1 = \sqrt{k^2 - k_{x_1}^2 - k_{y_1}^2}$$

$$s_2 = \sqrt{k^2 - k_{x_2}^2 - k_{y_2}^2}$$

Expression M

In Claim 4, Column 34, Lines 1-9, replace Expression I equation with the following equation:

$$\frac{1}{(2\pi)^3} \int_{-\infty}^{\infty}\int_{-\infty}^{\infty}\int_{-\infty}^{\infty} e^{-i(k_x x + k_{y_1} y_1 + k_y y)} a(k_x, k_{y_1}, k_y, k) e^{i\sqrt{(\sqrt{k^2 - k_{y_1}^2} + \sqrt{k^2 - k_y^2})^2 - k_x^2} z} dk_x dk_{y_1} dk_y$$

Expression I

In Claim 4, Column 34, Lines 10-19, replace Expression J equation with the following equation:

$$\phi(x, y, y_1, z, k) = \lim_{y_1 \to y} [\frac{1}{(2\pi)^3} \int_{-\infty}^{\infty}\int_{-\infty}^{\infty}\int_{-\infty}^{\infty} e^{-i(k_x x + k_{y_1} y_1 + k_y y)} a(k_x, k_{y_1}, k_y, k) e^{i\sqrt{(\sqrt{k^2 - k_{y_1}^2} + \sqrt{k^2 - k_y^2})^2 - k_x^2} z} dk_x dk_{y_1} dk_y]$$

Expression J

In Claim 6, Column 35, Lines 1-10, replace [Math 72] equation with the following equation:

$$\phi(x_1,x_2,y_1,y_2,z_1,z_2,\omega) = \iint_D \frac{e^{ik\rho_1}}{\rho_1}\frac{e^{ik\rho_2}}{\rho_2}\varepsilon(\xi,\eta,\zeta)d\xi d\eta d\zeta$$

$$\rho_1 = \sqrt{(x_1-\xi)^2+(y_1-\eta)^2+(z_1-\zeta)^2}$$

$$\rho_2 = \sqrt{(x_2-\xi)^2+(y_2-\eta)^2+(z_2-\zeta)^2}$$

Expression D

In Claim 6, Column 35, Lines 22, "surface; and are" should read --surface; $\xi$, $\eta$, and $\zeta$ are--

In Claim 6, Column 36, Lines 20-24, replace Expression M equation with the following equation:

$$s_1 = \sqrt{k^2 - k_{x_1}^2 - k_{y_1}^2}$$

$$s_2 = \sqrt{k^2 - k_{x_2}^2 - k_{y_2}^2}$$

Expression M